(12) United States Patent  
Jaffe et al.

(10) Patent No.: US 8,673,218 B2
(45) Date of Patent: *Mar. 18, 2014

(54) BIOANALYTICAL INSTRUMENTATION USING A LIGHT SOURCE SUBSYSTEM

(75) Inventors: Claudia B. Jaffe, Portland, OR (US); Steven M. Jaffe, Portland, OR (US); Michieal L. Jones, Davis, CA (US)

(73) Assignee: Lumencor, Inc., Beaverton, OR (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/486,404

(22) Filed: Jun. 1, 2012

(65) Prior Publication Data

US 2012/0238472 A1  Sep. 20, 2012

Related U.S. Application Data

(63) Continuation of application No. 12/938,224, filed on Nov. 2, 2010, which is a continuation of application No. 11/805,185, filed on May 21, 2007, now Pat. No. 7,846,391.

(60) Provisional application No. 60/802,883, filed on May 22, 2006, provisional application No. 60/831,011, filed on Jul. 14, 2006, provisional application No. 60/888,902, filed on Feb. 8, 2007.

(51) Int. Cl.
*G01N 21/64* (2006.01)
*G01N 21/66* (2006.01)

(52) U.S. Cl.
USPC .......... 422/82.08; 435/287.1; 435/287.2; 435/288.7; 435/283.1; 422/50; 422/82.05

(58) Field of Classification Search
USPC ........ 422/82.05, 50, 82.08; 435/283.1, 287.1, 435/287.2, 288.7
See application file for complete search history.

(56) References Cited

U.S. PATENT DOCUMENTS

| | | | |
|---|---|---|---|
| 1,998,054 | A | 4/1935 | McBurney |
| 3,313,337 | A | 4/1967 | Bernat |

(Continued)

FOREIGN PATENT DOCUMENTS

| | | |
|---|---|---|
| CA | 2 280 398 | 4/2000 |
| EP | 1 426 807 | 12/2003 |

(Continued)

OTHER PUBLICATIONS

Supplementary European Search Report dated Oct. 26, 2012 for European Patent Application No. 07797660.3, 8 pages.

(Continued)

*Primary Examiner* — Melanie Y Brown
(74) *Attorney, Agent, or Firm* — Fliesler Meyer LLP

(57) ABSTRACT

The invention relates to a light source for irradiating molecules present in a detection volume with one or more selected wavelengths of light and directing the fluorescence, absorbance, transmittance, scattering onto one or more detectors. Molecular interactions with the light allow for the identification and quantitation of participating chemical moieties in reactions utilizing physical or chemical tags, most typically fluorescent and chromophore labels. The invention can also use the light source to separately and simultaneously irradiate a plurality of capillaries or other flow confining structures with one or more selected wavelengths of light and separately and simultaneously detect fluorescence produced within the capillaries or other flow confining structures. In various embodiments, the flow confining structures can allow separation or transportation of molecules and include capillary, micro bore and milli bore flow systems. The capillaries are used to separate molecules that are chemically tagged with appropriate fluorescent or chromophore groups.

24 Claims, 16 Drawing Sheets

(56) References Cited

U.S. PATENT DOCUMENTS

| | | |
|---|---|---|
| 3,637,285 A | 1/1972 | Stewart |
| 3,759,604 A | 9/1973 | Thelen |
| 3,881,800 A | 5/1975 | Friesem |
| 3,982,151 A | 9/1976 | Ludovici |
| 4,003,080 A | 1/1977 | Maiman |
| 4,298,820 A | 11/1981 | Bongers |
| 4,371,897 A | 2/1983 | Kramer |
| 4,510,555 A | 4/1985 | Mori |
| 4,539,687 A | 9/1985 | Gordon |
| 4,602,281 A | 7/1986 | Nagasaki et al. |
| 4,626,068 A | 12/1986 | Caldwell |
| 4,642,695 A | 2/1987 | Iwasaki |
| 4,644,141 A | 2/1987 | Hagen |
| 4,657,013 A | 4/1987 | Hoerenz et al. |
| 4,695,332 A | 9/1987 | Gordon |
| 4,695,732 A | 9/1987 | Ward |
| 4,695,762 A | 9/1987 | Berkstresser |
| 4,713,577 A | 12/1987 | Gualtieri |
| 4,724,356 A | 2/1988 | Daehler |
| 4,798,994 A | 1/1989 | Rijpers |
| 4,804,850 A | 2/1989 | Norrish et al. |
| 4,852,985 A | 8/1989 | Fujihara et al. |
| 4,937,661 A | 6/1990 | Van Der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza et al. |
| 5,803,579 A | 9/1998 | Turnbull et al. |
| 5,804,919 A | 9/1998 | Jacobsen |
| 5,808,759 A | 9/1998 | Okamori et al. |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,891,656 A | 4/1999 | Zarling et al. |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu |
| 6,614,161 B1 | 9/2003 | Jacobsen et al. |
| 6,614,179 B1 | 9/2003 | Shimizu et al. |
| 6,637,905 B1 | 10/2003 | Ng |
| 6,642,652 B2 | 11/2003 | Collins |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler et al. |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rains, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |
| 7,083,610 B1 | 8/2006 | Murray et al. |
| 7,141,801 B2 | 11/2006 | Goodwin |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 | 1/2008 | Rutherford et al. |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |
| 7,467,885 B2 | 12/2008 | Grotsch et al. |
| 7,488,088 B2 | 2/2009 | Brukilacchio |
| 7,488,101 B2 | 2/2009 | Brukilacchio |
| 7,498,734 B2 | 3/2009 | Suehiro et al. |
| 7,540,616 B2 | 6/2009 | Conner |
| 7,595,513 B2 | 9/2009 | Plank et al. |
| 7,633,093 B2 | 12/2009 | Blonder et al. |
| 7,709,811 B2 | 5/2010 | Conner |
| 7,746,560 B2 | 6/2010 | Yamazaki |
| 7,832,878 B2 | 11/2010 | Brukilacchio |
| 7,837,348 B2 | 11/2010 | Narendran et al. |
| 7,854,514 B2 | 12/2010 | Conner |
| 7,857,457 B2 | 12/2010 | Rutherford et al. |
| 7,976,307 B2 | 7/2011 | Plank et al. |
| 8,029,142 B2 | 10/2011 | Conner |
| 2001/0055208 A1 | 12/2001 | Kimura |

(56) References Cited

U.S. PATENT DOCUMENTS

| | | | |
|---|---|---|---|
| 2002/0109844 | A1 | 8/2002 | Christel et al. |
| 2002/0127224 | A1 | 9/2002 | Chen |
| 2003/0044160 | A1 | 3/2003 | Jonese et al. |
| 2003/0095401 | A1 | 5/2003 | Hanson et al. |
| 2003/0127609 | A1 | 7/2003 | El-Hage et al. |
| 2003/0160151 | A1 | 8/2003 | Zarate et al. |
| 2003/0230728 | A1 | 12/2003 | Dai |
| 2003/0233138 | A1 | 12/2003 | Spooner |
| 2004/0090600 | A1 | 5/2004 | Blei |
| 2004/0090794 | A1 | 5/2004 | Ollett et al. |
| 2004/0247861 | A1 | 12/2004 | Naasani |
| 2005/0062404 | A1 | 3/2005 | Jones et al. |
| 2005/0116635 | A1 | 6/2005 | Walson et al. |
| 2005/0146652 | A1 | 7/2005 | Yokoyama et al. |
| 2005/0152029 | A1 | 7/2005 | Endo |
| 2005/0184651 | A1 | 8/2005 | Cheng |
| 2005/0201899 | A1 | 9/2005 | Weisbuch |
| 2005/0248839 | A1 | 11/2005 | Yamaguchi |
| 2005/0260676 | A1 | 11/2005 | Chandler |
| 2005/0263679 | A1 | 12/2005 | Fan |
| 2006/0002131 | A1 | 1/2006 | Schultz et al. |
| 2006/0030026 | A1 | 2/2006 | Garcia |
| 2006/0060872 | A1 | 3/2006 | Edmond et al. |
| 2006/0060879 | A1 | 3/2006 | Edmond |
| 2006/0114960 | A1 | 6/2006 | Snee |
| 2006/0170931 | A1 | 8/2006 | Guo |
| 2006/0237658 | A1 | 10/2006 | Waluszko |
| 2006/0282137 | A1 | 12/2006 | Nightingale et al. |
| 2007/0053184 | A1 | 3/2007 | Brukilacchio |
| 2007/0053200 | A1 | 3/2007 | Brukilacchio |
| 2007/0058389 | A1 | 3/2007 | Brukilacchio |
| 2007/0064202 | A1 | 3/2007 | Moffat et al. |
| 2007/0086006 | A1 | 4/2007 | Ebersole et al. |
| 2007/0126017 | A1 | 6/2007 | Krames et al. |
| 2007/0211460 | A1 | 9/2007 | Ravkin |
| 2007/0253733 | A1 | 11/2007 | Fey |
| 2007/0279914 | A1 | 12/2007 | Rutherford et al. |
| 2007/0279915 | A1 | 12/2007 | Rutherford et al. |
| 2007/0280622 | A1 | 12/2007 | Rutherford et al. |
| 2007/0281322 | A1 | 12/2007 | Jaffe et al. |
| 2007/0284513 | A1 | 12/2007 | Fan |
| 2007/0297049 | A1 | 12/2007 | Schadwinkel et al. |
| 2008/0079910 | A1 | 4/2008 | Rutherford et al. |
| 2008/0224024 | A1 | 9/2008 | Ashdown |
| 2008/0291446 | A1 | 11/2008 | Smith |
| 2009/0122533 | A1 | 5/2009 | Brukilacchio |
| 2009/0196046 | A1 | 8/2009 | Rutherford et al. |
| 2009/0268461 | A1 | 10/2009 | Deak et al. |
| 2010/0188017 | A1 | 7/2010 | Brukilacchio |

FOREIGN PATENT DOCUMENTS

| | | |
|---|---|---|
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| KR | 20-1999-0041018 | 12/1999 |
| KR | 10-2006-0055934 | 5/2006 |
| KR | 10-2006-0089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report dated Dec. 31, 2008, Application No. PCT/US2008/072394, 10 pages.

International Search Report for PCT/US2010021843 dated Aug. 19, 2010, 9 pages.

Extended European Search Report for PCT/US2008072394 dated Oct. 7, 2011, 9 pages.

Lauer, Herbert F., "Exposure Meter for Precision Light Dosage", The Review of Scientific Instruments, vol. 20, No. 2, Feb. 1949, pp. 103-109.

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Vlasenko, N.A., et al., "Interference of Luminescent Emission from an Evaporated Phosphor," Opt. Spect., vol. 11, pp. 216-219 (1961).

Vlasenko, N.A., et al., "Investigation of Interference Effects in Thin Electroluminescent ZnS—Mn Films," Opt. Spect., vol. 28, pp. 68-71 (1970).

Poelman, D., et al., "Spectral Shifts in Thin Film Electroluminescent Devices: An Interference Effect," J. Phys. D: Appl. Phys., vol. 25, pp. 1010-1013 (1992).

Tuenge, R.T., "Current Status of Color TFEL Phosphors," Electroluminescence—Proceedings of the Sixth International Workshop on Electroluminescence, El Paso, Tex., pp. 173-177, May 1992.

Plasma Display Manufacturers of the American Display Consortium, "Recommended Research Topics on Plasma Display for the DARPA Sponsored Phosphor Center of Excellence," pp. 1-2, Mar. 24, 1993.

Yamamoto, Y., et al., "Optical Processes in Microcavities," Physics Today, pp. 66-73, Jun. 1993.

E.F. Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.

Yokoyama, H., "Physics and Device Applications of Optical Microcavities," Science, vol. 256, pp. 66-70, Apr. 3, 1992.

Haroche, S., et al., "Cavity Quantum Electrodynamics," Scientific American, pp. 54-62, Apr. 1993.

Depp, S.W., et al., "Flat Panel Displays," Scientific American, pp. 90-97, Mar. 1993.

Huo, D.T.C., et al., "Reticulated Single-Crystal Luminescent Screen," J. Electrochem. Soc., vol. 133, No. 7, pp. 1492-1497, Jul. 1986.

Hinds, E.A., "Spectroscopy of Atoms in a Micron-Sized Cavity," (date and periodical title unknown), pp. 18-19.

Whitaker, Jerry C., "Electronic Displays: Technology, Design, and Applications," McGraw-Hill, Inc., pp. 185-192 (1994).

Hecht, Jeff, "Diverse fiberoptic systems require varied sources," Laser Focus World, vol. 36, No. 1, pp. 155-161, Jan. 2000.

Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.

World Watch, Photonics Spectra, "IR Reflective Coating Boosts Bulb's Output, Recycling of IR Energy Saves Power, Cuts Costs" pp. 40-41, Jan. 1991.

Jenmar Visual Systems, Sunnyvale, CA, 4 pages, no date, but at least as early as Oct. 15, 1998.

DDS™ Rear Projection Screens, LORS™ Reflection Screens, © 1998 Physical Optics Corporation, Torrance, CA, 2 pages.

Schott Glass Technologies, Inc., Schott Total Customer Care, Contrast Enhancement Filters, Duryea, PA, 6 pages, Jan. 1998.

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Young, L., "Multilayer Interference Filters with Narrow Stop Bands," Applied Optics, vol. 6, No. 2, pp. 297-312, Feb. 1967.

Hemingway, D.J. and Lissberger, P.H., "Effective Refractive Indices of Metal-Dielectric Interference Filters," Applied Optics, vol. 6, No. 3, pp. 471-476, Mar. 1967.

Holloway, R.J. and Lissberger, P.H., "The Design and Preparation of Induced Transmission Filters," Applied Optics, vol. 8, No. 3, pp. 653-660, Mar. 1969.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

(56) References Cited

OTHER PUBLICATIONS

Lissberger, P.H., "Coatings with Induced Transmission," Applied Optics, vol. 20, No. 1, pp. 95-103, Jan. 1, 1981.

Pelletier, E. and MacLeod, H.A., "Interference Filters with Multiple Peaks," Journal of the Optical Society of America, vol. 72, No. 6, pp. 683-687, Jun. 1982.

Da-Lite Screen Company, Inc., www.da-lite.com, 46 pages website downloads as of Oct. 8, 1998.

Stewart Filmscreen Corporation®, www.stewartfilm.com, 34 pages website downloads as of Oct. 8, 1998.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

Deck, L., et al., "Two color light-emitting-diode source for high precision phase-shifting interferometry", Optics Letters, vol. 18, No. 22, Nov. 15, 1993, pp. 1899-1901.

Morgan, C. G., et al., "New Approaches to Lifetime-Resolved Luminescence Imaging", Journal of Fluorescence, vol. 7, No. 1, 1997, pp. 65-73.

International Search Report dated Sep. 4, 2013 for Application No. PCT/US2013/043134, 11 pages.

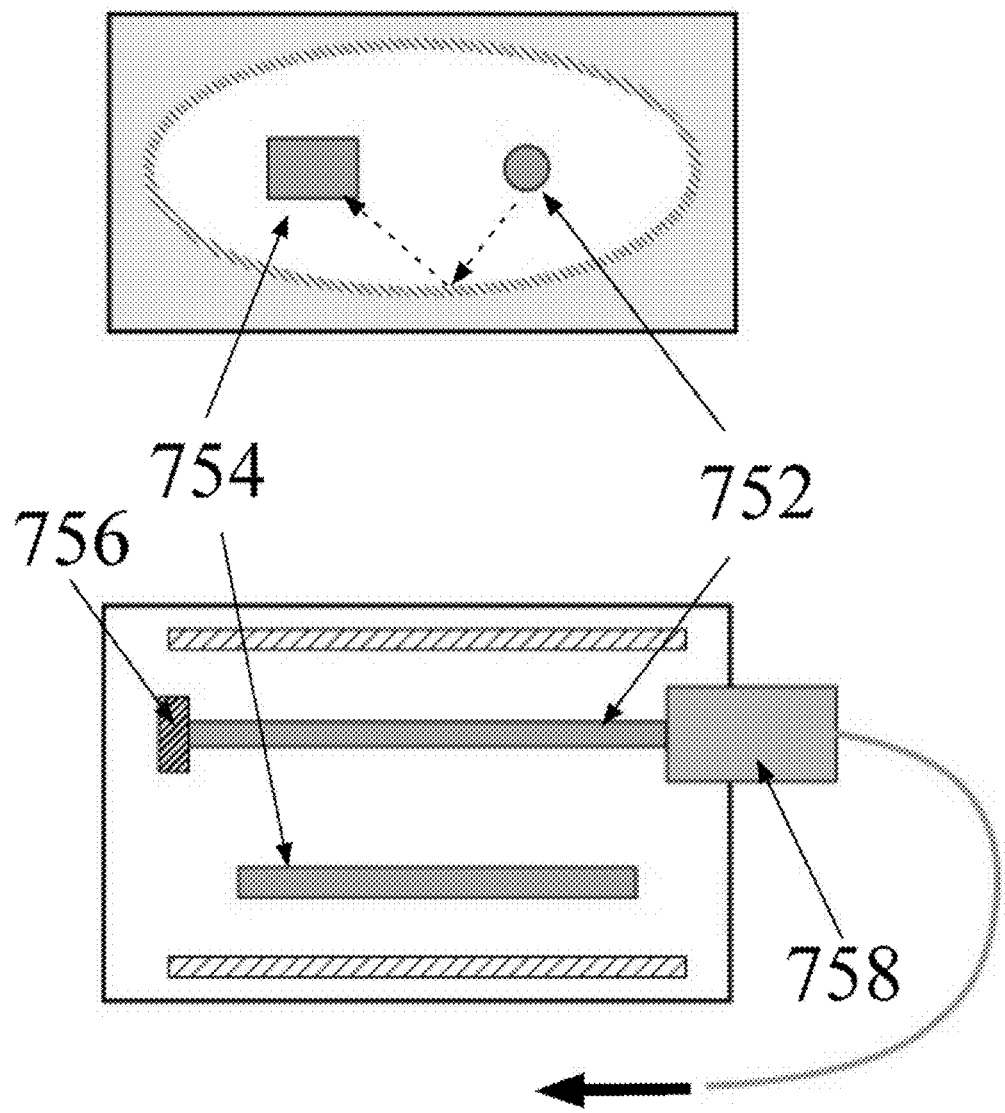

BIOANALYTICAL INSTRUMENTATION USING A LIGHT SOURCE SUBSYSTEM

CLAIM OF PRIORITY

This application is a continuation of U.S. Patent Application titled "BIOANALYTICAL INTRUMENTATION USING A LIGHT SOURCE SUBSYSTEM", application Ser. No. 12/938,224, filed Nov. 2, 2010 which is a continuation of U.S. Patent Application titled "BIOANALYTICAL INTRUMENTATION USING A LIGHT SOURCE SUBSYSTEM", application Ser. No. 11/805,185, filed May 21, 2007 (now U.S. Pat. No. 7,846,391); which claims the benefit of priority to U.S. Provisional Patent Application titled "CAPILLARY ELECTROPHORESIS LIGHT PIPE", Application No. 60/802,883, filed May 22, 2006; U.S. Provisional Patent Application titled "WELL LIGHT PIPE", Application No. 60/831,011, filed Jul. 14, 2006; and U.S. Provisional Patent Application titled "CAPILLARY ELECTROPHORESIS LIGHT SOURCE SUBSYSTEM", Application No. 60/888,902, filed Feb. 8, 2007; each of which applications are herein incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to luminescence systems for irradiating bioanalytical instrumentation including wells containing chemicals for inducing reactions or detecting reactants or products of chemical reactions. The bioanalytical instrumentation can include a light source and fiber optic systems for irradiating analytes within capillaries with selected wavelengths of light and detecting luminescence produced by the analytes within the capillaries.

BACKGROUND

The micro titer plate reader has been a workhorse for bioanalytical testing for decades. It enables the facile and rapid interrogation of an array of chemical reactions. Typically 8 by 12 well formats of 96 wells are filled with reagents and or products of a colorimetric or fluorescent reaction. Higher order formats include multiples of 96 wells. Such micro-titer plates are exposed to light of a desired wavelength and the interaction of the reacting species with the light is recorded.

Reactions may be immunochemical, enzyme based, polymerizations, intercollations or any of the varied molecular biological and biochemical systems investigated in the biochemists' laboratory. The interactions may include and are not limited to absorbance, transmittance, scatter and fluorescence. Micro titer plate readers are designed to generate one or more wavelengths of interest. Typically the light is generated using a wide spectrum source, arc lamps and halogen bulbs with numerous filters or gratings are common design components.

Biochemical reactions formatted in either homogeneous or heterogeneous based detection platforms are also performed in miniaturized systems, e.g. on micro fluidic chips and micro arrays. In miniaturized systems, reaction volumes are contained within channels and/or with carefully modified surface chemistry to allow for a plethora of chemical and biological analysis in small reaction volumes. The chemistry is typically interrogated using confocal microscopy or imaging to assess the extent of higher density features. Tens to hundreds of thousands of enzyme, immunochemical, nucleic acid and protein reactions can be followed simultaneously. Lamp and lasers power the various detection systems designed to report on the extent of reaction.

One now commonplace procedure performed in the bioanalytical laboratory is the polymerase chain reaction (PCR). The technique has become fundamental to molecular biology. It is one of a family of methods (i.e. reverse transcriptase PCR) for synthesizing a given quantity of pre-selected biopolymer. PCR functions on DNA. In a typical experiment, the DNA of interest is separated into two complementary strands. The ends of each strand bind to a primer at the end where the synthesis begins. The addition of the DNA polymerase initiates the synthesis of a complementary strand on each single strand creating a doubling of the amount of DNA. The process is repeated until a sufficient number of DNA segments have been synthesized. A unique temperature profile is used to advance the reaction through the phases of separation (melting), primer binding (annealing), and replication (extension). While the PCR technique has become a workhorse of the biotechnologist due to the enhanced sensitivity it offers over blotting techniques, PCR is not ideally suited to quantitation. Small differences between sample sizes can become huge differences in final amplified material after multiple doublings.

A typical PCR reaction can be seen in three phases: an early lag phase, an exponential growth phase and a plateau region. The lag phase is a consequence of the sensitivity of the instrument and the background signal of the probe system used to detect the PCR product. The exponential growth phase commences when sufficient product has accumulated to be detected by the specific instrument. During this exponential growth the amplification is described by $T_n = T_i(E)^n$, where $T_n$ is the amount of target sequence at cycle n, $T_i$ is the initial amount of target material, and E is the efficiency of amplification. In the final plateau phase the amplification efficiency drops as product competes more effectively with primers for annealing and the amount of enzyme becomes limiting. The exponential equation no longer holds in the plateau phase. Most of the quantitative information is found in the exponential cycles but the exponential cycles typically comprise only 4 or cycles out of 40. For traditional PCR methods, identifying the exponential cycles requires the reaction be split into multiple reaction tubes that are assayed for PCR product after varying numbers of cycles. This requires either assaying many tubes or having a fairly good idea of the answer before the experiment is begun. Once the position of this phase is determined the experimental phase can be compared to known standards and the copy number can be calculated.

Instrumentation advancements have made real-time monitoring of PCR reactions possible. Thermocycling is carried out using standard techniques known to those skilled in the art, including rapid cycling PCR. Fluorescence monitoring at each cycle for quantitative PCR was developed by Higuchi et al., "Simultaneous Amplification and Detection of Specific DNA Sequences," Bio. Technology, 10:413-417, 1992, which is herein expressly incorporated by reference in its entirety. Ethidium bromide was used as the fluorescent entity. Fluorescence was acquired once per cycle for a relative measure of product concentration. The cycle where observable fluorescence first appeared above the background fluorescence correlated with the starting copy number, allowing the construction of a standard curve. Alternatively PCR amplification may be conducted with fluorescently labeled hybridization probes. The hybridization probe system comprises two oligonucleotide probes that hybridize to adjacent regions of a DNA sequence wherein each oligonucleotide probe is labeled with a respective member of a fluorescent energy transfer pair. In this embodiment, the presence of the target nucleic acid sequence in a biological sample is detected by measuring fluorescent energy transfer between the two-labeled oligonucleotides. A number of strategies now exist using molecular beacons or intercollating dyes all of which are strategies to increase signal as a function of increasing DNA concentration as the synthesis cycles increase.

Such instrumentation and fluorescent monitoring techniques have made kinetic PCR significantly easier than traditional competitive PCR. The ease, accuracy and precision of quantitative PCR have all improved by allowing observation of the PCR product concentration at every cycle. In the Roche® Diagnostics embodiment of the kinetic PCR instrument, PCR reactions are conducted using the Light Cycler®, a real-time PCR instrument that combines a rapid thermal cycler with a fluorimeter. Through the use of such a device, PCR product is detected with fluorescence and no additional sample processing, membrane arrays, gels, capillaries, or other analytical tools are necessary. Other PCR instrumentation as known in the art may be used in the practice of the present invention.

Separation by electrophoresis is based on differences in solute velocity in an electric field. The velocity of a charged analyte is a function of its electrophoretic mobility and the applied voltage. The method of electrophoresis is used in a number of different techniques including capillary gel electrophoresis, capillary zone electrophoresis, micellar electrokinetic chromatography, capillary electro chromatography, isotachophoresis and isoelectric focusing.

In general, the mobility of an analyte in a particular medium is constant and characteristic of that analyte. The analytes mobility is a result of two factors. The analyte is attracted to the electrode of opposite charge, pulling it through the medium. At the same time, however, frictional forces try to prevent the analyte moving toward the charge. The balance of these forces determines the actual overall mobility of the analyte. An analytes size, polarity and number of electric charge(s), relative hydrophobicity and ionic strength determine how rapidly an electric field can move the analyte through a medium. A buffer is used to assist the flow of the analyte relative to the field. The buffer's chemical composition, pH, temperature and concentration alter the mobility of the analyte. Many important biological molecules such as amino acids, peptides, proteins, nucleotides, and nucleic acids, posses ionizable groups and, therefore, at any given pH, exist in solution as electrically charged species either as cations containing a positive (+) charge or as anions containing a negative (−) charge. Depending on the nature of the net charge, the charged particles will migrate either to the cathode or to the anode. A small analyte will have less frictional drag than a large analyte and hence move through the medium faster than a large analyte. Similarly, a multiply charged analyte will experience more attraction to the electrode and also move through the medium faster than a singly charged analyte. It is this difference in solute velocities that is responsible for the separating effect in electrophoresis that results in resolution of the species detected.

Gel electrophoresis is a method that separates molecules such as DNA or proteins on the basis of their physical properties. A gel is a solid colloid. Thus, gel electrophoresis refers to the technique in which molecules are forced to cross a span of gel, motivated by an electrical current. Activated electrodes at either end of the gel provide the electric field and thus the driving force for the migration of the analyte. During electrophoresis, molecules are forced to move through the pores in the gel when the electrical current is applied. Their rate of migration, through the induced electric field, depends on the strength of the field, their charge, their size and the shape of the molecules, the relative hydrophobicity of the molecules, and on the ionic strength and temperature of the buffer in which the molecules are moving.

One use of gel electrophoresis is the identification of particular DNA molecules by the band patterns they yield in gel electrophoresis, after being cut with various restriction enzymes. Viral DNA, plasmid DNA, and particular segments of chromosomal DNA can all be identified in this way. Another use is the isolation and purification of individual DNA fragments containing interesting genes, which can be recovered from the gel with full biological activity.

Capillary Zone Electrophoresis (CZE) replaces the gel in gel electrophoresis with the combination of a buffer and a solid support contained within the capillary. In CZE, the analyte must move through the solid support contained within the capillary under the action of the buffer, which is charged by the applied electric field. The buffer's chemical nature, pH, temperature, concentration and the presence of surfactant additives can be selected to assist in fully resolving (i.e., spatially separating different analytes in the capillary with respect to the time from introduction of the sample) different analytes in space (position in the capillary) with respect to time. Analytes separated by CZE can be detected based on absorption or fluorescence. Detection can be carried out using on-column or fiber optic Z-cells.

In addition to electrophoretic techniques, separation of molecules can be carried out in the absence of an applied field using chromatographic techniques. In liquid chromatography, the molecule dissolved in a buffer can still be charged, but rather than an electric field creating the driving force, molecule migration is dependent on the flow of the buffer. Frictional forces due to the interaction of the molecule with a solid support present in a column, act to prevent the molecule from moving with the buffer. The molecule's size, hydrophobicity, and ionic strength determine how rapidly the buffer can move the molecule through a medium. The buffer's chemical composition, pH, temperature and concentration together with the nature of the solid support dispersed in the column alter the mobility of the molecule. High performance liquid chromatography (HPLC) utilizes pumps to increase the flow of buffer through the columns resulting in high column backpressure, improved resolution, increased flow rates and reduced analysis times. By reducing the diameter of the column and/or increasing the length of the column the resolution can be improved. However, a problem with narrower columns (milli bore or micro bore) involves detection of the eluted species. As the diameter of the capillary in the narrow bore HPLC systems is further reduced, only a small number of molecules are available for detection in a small-defined area.

Microfluidic systems comprised of microfluidic chips, automated reagent delivery apparatus and detection instrumentation are designed to minimize the users' effort in reagent delivery, reagent dilution and/or mixing, initiating chemical reactions and detecting those chemical reactions in small volumes within highly automated environments. Among the numerous applications that exist, fluorescence is a commonly used detection format. It is a sensitive and robust method for detecting enzyme assays, immunoassays, polymerase chain reaction (PCR), quantitative PCR, genomic sequencing among many other important chemical reactions. Both homogeneous and heterogeneous reactions are suited to such devices and analysis is not limited by whether the reaction takes place in free solution or on a solid support or within a narrow pore. Often microfluidic devices are produced by etching, molding or embossing channels and wells into solid substrates (glass, silicon, plastic, etc.). Numerous layers of the device can be fabricated and then the layers assembled to form the final analysis tool. Channels can be etched in single or multiple dimensions enabling more complicated chemical separation and detection. Such devices can be used to introduce reagents directly onto the chip or interfaced with automation equipment for such purposes. Like all fluorogenic detection, these systems require an excitation source.

SUMMARY

Light based detection systems utilizing the processes described above have long been workhorses of chromatography systems and reaction vessels including microarray scanners, microtiter plate readers, DNA sequencers, PCR and Q-PCR instruments, fluorescent microscopes, flow cytometery instruments and lab on a chip devices used in drug discovery and other life-sciences research. Light sources are integral components of these bioanalytical tools. However, the lamps and lasers that power these bioanalytical systems have presented engineering and cost constraints that limit sensitivity, reproducibility and robustness.

The present invention consists of one or more light sources in the form of a luminescent light pipe referred to herein as a lamp, in conjunction with relay optics for luminescence collection from an analyte forming a luminescence system for a volume interrogation apparatus wherein the interaction of light with a chemical species located within or supported on a solution volume can be the measure of the presence or quantitation of an analyte. Luminescence is defined as light not generated by high temperature alone, typical of incandescence, including but not limited to fluorescence and phosphorescence. Where high temperatures are defined as above approximately 2000° K. The analyte can be part of a reaction involving species including biopolymers such as, oligonucleotides (DNA, RNA iRNA, siRNA), proteins (including antibodies, enzymes, agonists, antigens, hormones, toxins), oligosaccharides and non polymeric species such as steroids, lipids, phospholipids, small organic signaling molecules (e.g., retinoic acid), pesticides and non peptidic toxins, hormones and antigens.

In alternative embodiments of the present invention, a lamp, in conjunction with relay optics for luminescence collection, form a flexible and efficient luminescence system for a capillary/fluorescence apparatus. In an embodiment of the invention, a plurality of light sources and fiber optic systems separately and simultaneously irradiate a plurality of capillaries with selected wavelengths of light and the fluorescence produced by the molecules flowing within the capillaries can be separately and simultaneously detected.

While lamps and lasers are key components in the biochemical reactor instrument design each is best suited to unique applications with compromises based on inherent performance traits. Typically lamps produce broad-spectrum spontaneous emission but due to their large angular output collection efficiency is poor. Large power densities are difficult to attain; moreover accessing discrete wavelengths using filters and lenses results in dramatic power losses. Lasers can produce large power outputs at discrete wavelengths based on stimulated emission; however, intensity and spatial modulation is difficult and costly. As well, the number of available discrete wavelengths is limited. The design and cost effective production of bench top and point-of-care analyzers is limited by this current pool of light generators.

Traditional lamps and lasers are the most frequently employed light generators in bioanalytical microfluidic instrumentation. While lamps and lasers are key components in the instrument design each is best suited to unique applications with compromises based on inherent performance traits. Typically lamps produce broad-spectrum spontaneous emission but due to their large angular output, collection efficiency is poor. Further, large power densities are difficult to attain. Moreover, accessing discrete wavelengths using filters and lenses results in dramatic power losses. Lasers can produce large power outputs at discrete wavelengths based on stimulated emission, however, intensity and spatial modulation is difficult and costly. In addition, the number of available discrete wavelengths is limited. The design and cost effective production of bench top and point-of-care analyzers is limited by the current light generators.

Lamp

In various embodiments of the present invention, a lamp emits wavelengths of light, which excite fluorescence from photosensitive targets in the sample of interest. In various embodiments of the present invention, a lamp can be in the form of a tube, rod, or fiber of varying or constant diameter and varying or constant curvature. The cross section can be circular, square or rectangular and can be constant or varying. In various embodiments of the present invention, a constituent light pipe can be made of glass, plastic, single or multiple inorganic crystal(s), or a confined liquid. In various embodiments of the present invention, a pipe either contains or can be coated with a layer or layers containing, a narrow band luminescent material such as organic or inorganic compounds involving rare earths, transition metals or donor-acceptor pairs. In various embodiments of the present invention, a lamp emits confined luminescence when excited by IR, UV, or visible light from an LED, laser, fluorescent tube, arc lamp, incandescent lamp or other light source. In an embodiment of the present invention, a lamp operates through the process of spontaneous emission, which results in a much larger selection of available wavelengths than can be available for efficient stimulated emission (laser action). In an alternative embodiment, electrons or other radiation are used to excite the activator and thereby the light pipe.

In an embodiment of the invention, light pipes will incorporate organic luminescent material referred to as plastic scintillators, doped or activated plastic optical fibers or wavelength shifting plastics as described by Albrecht, M. et al., in "Scintillators and Wavelength Shifters for the Detection of Ionizing Radiation", Nuclear Science Symposium Conference Record, 2003 IEEE, Volume 2, Issue: 19-25 Oct. (2003) 1086 and Pla-Dalmau, A. et al., "Low-cost extruded Plastic Scintillator", Nuclear Instruments and Methods in Physics Research A, 466 (2001) 482 both of which are hereby expressly incorporated by reference in their entireties. These materials are commercially available through Kuraray, Saint-Gobain and Eljen Technology. The host material can be typically made from polymethylmethacrylate or acrylic (PMMA), polyvinyltoluene, or polystyrene. There are numerous fluorescing dopants available enabling these materials to emit across the visible from 400 to 650 nm. The best dopant for the Argon Ion laser replacement is K27. The plastic material can take on any geometric shape including uncladded fiber, cladded fiber, tubes and rods with circular, square or rectangular cross section which can be constant or varying.

The tubes and rods can have constant or varying curvature and have a constant or varying diameter.

Relay Optics

In an embodiment of the present invention, relay optics consist of light pipes, optical fibers, lenses and filters, which optically transport the light from a lamp to one or more capillaries and light pipes, optical fibers, lenses and filters which collect and transport any generated fluorescence to an appropriate detector or array of detectors, in conjunction with adaptors for coupling the excitation light into the capillaries, coupling the emission light out of the capillaries and for enhancing physical discrimination of the excitation and emission. In an embodiment of the present invention, relay optics, including fibers, can be constructed in a loop or as a cavity so that light from a lamp can pass through one or more capillaries multiple times to enhance excitation efficiency.

In an embodiment of the present invention, a number of lamps each emitting one or more color of light can have their constituent light pipes coupled in parallel or in series acting to produce multiple colors simultaneously or in sequence. In an embodiment of the present invention, one or more lamps can illuminate single channels, multiple parallel channels, multiple channels in multiple dimensions, numerous spots along the analysis channel and/or reservoirs connected to the flow streams.

In an embodiment of the present invention, lamps can be irradiated continuously during the measurement process or can be pulsed on and off rapidly to enable time-based detection methods. In an embodiment of the present invention, a lamp can be switched off between measurements, to eliminate the heat output. This can be contrasted with alternatives such as arc lamps or lasers that are unstable unless they are operated continuously.

Luminescence and Collection System

In an embodiment of the present invention, a flexible luminescence and collection system for capillary/fluorescence apparatus allows for a varying number of samples to be analyzed simultaneously. 'Simultaneously' is herein defined as occurring close in time. Two light pipes can irradiate two capillaries at the same time and the fluorescence from the molecules in one of the capillaries can be delayed due to physical or chemical effects relating to absorption, phosphorescence and/or fluorescence resulting in a delay in the fluorescence from the molecules in one of the capillaries. This excitation can be still considered to result in 'simultaneous detection'. In an embodiment of the present invention, a luminescence and collection system can be adjusted for uniform luminescence of multiple capillaries or wells or a large area including numerous wells, spots or channels as 'detection volumes'. In an embodiment of the present invention, luminescence systems can irradiate an array of channels in an array of capillaries. In an embodiment of the present invention, an array of channels can be etched, molded, embossed into the capillaries. In an embodiment of the present invention, a set of wells intimately connected to fluidic conduits can be stepped along the length of the fluidic conduit such that they can be interrogated at numerous sites for the purposes of creating a map or image of the reacting species.

In an embodiment of the present invention, a luminescence and collection system can irradiate an array of wells, spots and or an array of channels (be they etched, molded or embossed) or a set of wells intimately connected to fluidic conduits such that they can be interrogated at numerous sites for the purposes of creating a map or image of the reacting species.

In an embodiment of the present invention, a luminescence and collection system can irradiate homogeneous reactions within fluidic conduits or reservoirs; to irradiate heterogeneous reactions on the surface of fluidic conduits or reservoirs; to irradiate homogeneous or heterogeneous reactions on the surface of or within the pores of a porous reaction support.

In an embodiment of the present invention, a luminescence and collection system can emit multiple colors as desired. In an embodiment of the present invention, a luminescence and collection system can be pulsed on and off as desired to reduce heat generation. In an embodiment of the present invention, a luminescence and collection system can be pulsed on and off to allow time-based fluorescence detection.

In an embodiment of the present invention, a luminescence and collection system can detect one or a number of reactions within the detected volume or volumes. The narrow band source of the light pipe driven analyzer provides better specificity, higher sensitivity, and lower backgrounds signals. The light pipe driven analyzer easily accommodates multiple wavelengths by additions of serially connected components.

In an embodiment of the present invention, a luminescence and collection system can be pulsed on an off as desired to reduce or control heat generation and to allow time-based fluorescence detection.

In an embodiment of the present invention, luminescence systems can irradiate homogeneous reactions within fluidic conduits or reservoirs. In an embodiment of the present invention, luminescence systems can irradiate heterogeneous reactions on the surface of fluidic conduits or reservoirs. In an embodiment of the present invention, luminescence systems can irradiate homogeneous or heterogeneous reactions on the surface of or within the pores of a porous reaction support.

Other objects and advantages of the present invention will become apparent to those skilled in the art from the following description of the various embodiments, when read in light of the accompanying drawings.

BRIEF DESCRIPTION OF THE FIGURES

Various embodiments of the present invention can be described in detail based on the following figures, wherein:

FIG. 7A shows a schematic drawing (side view) illustrating an elliptical reflector with a luminescent light pipe positioned at one focus of the ellipse and a linear array of LED's positioned at the other focus of the ellipse;

FIG. 7B shows a schematic drawing (top view) illustrating an elliptical reflector with a luminescent light positioned at one focus of the ellipse and a linear array of LED's positioned at the other focus of the ellipse;

DETAILED DESCRIPTION

Figure 9:
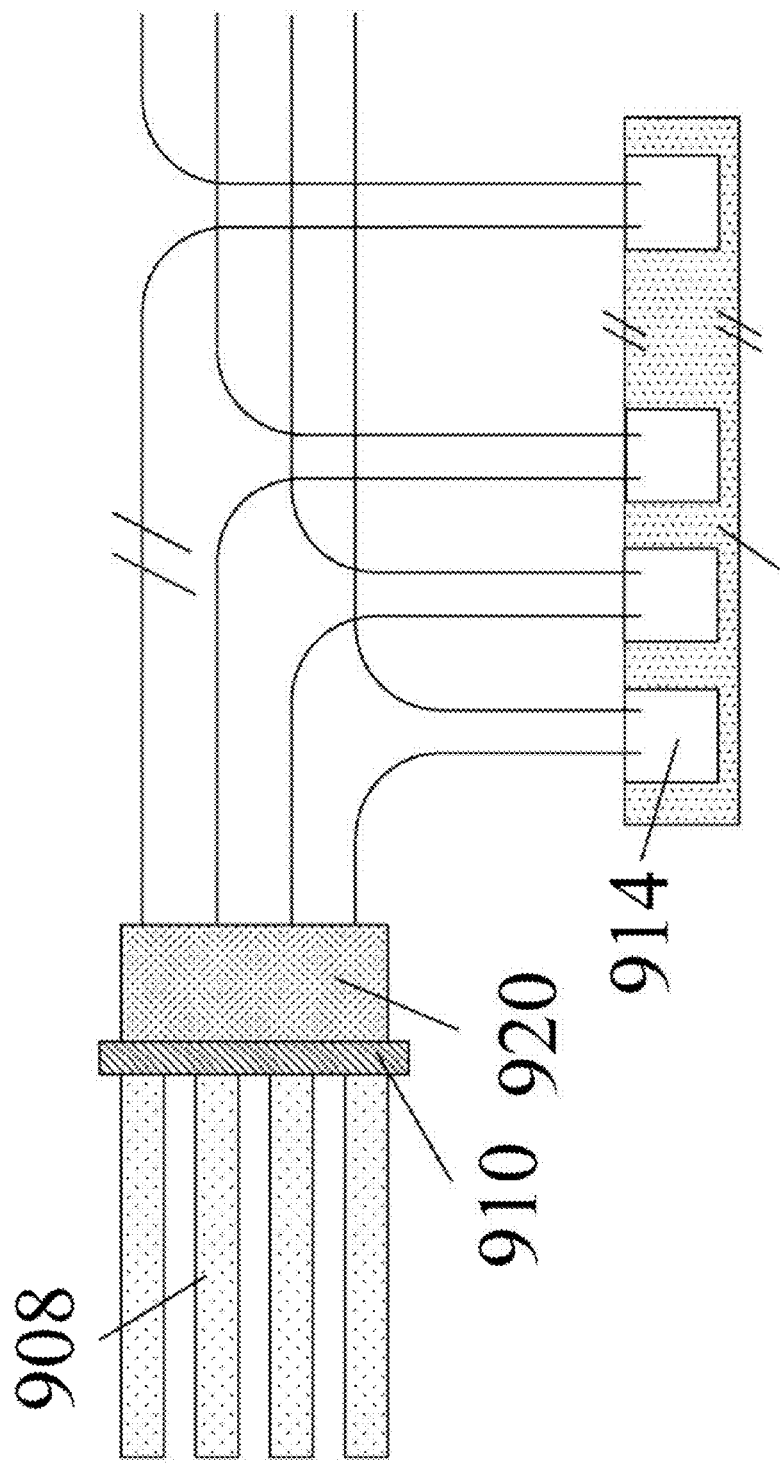
FIG. 9 shows a schematic drawing of system with multiple luminescent light pipes connected to optical fibers which provide emission to each well and separate fibers that collect emission from each well.

The detection volume in the form of a well of fluid, a spot of fluid, a channel containing fluid or a reservoir attached to a channel containing fluid will all be referred to herein as the "detection volume". The term "detection volume" can also refer to any of the afore mentioned constructs in which the reaction for detection occurs in freely diffusing solution, in a gel or polymer, attached to a surface, contained within a pore, or in some subsection of the entire well volume. As seen in FIG. 9, one example of the present invention comprises a plurality of lamps (908) with filters (910) for selecting the wavelength of choice, in conjunction with a device for coupling (920) the lamps into multiple optical fibers, multiple optical fibers for transferring the excitation light to the wells, adapters for coupling light from the fibers into the detection volumes (914) located in a microtiter plate (924) and for coupling fluorescence from the detection volumes into collection fibers, and collection fibers for transferring the emitted light to a detector array. The term "emitted light" is defined as including fluorescence, phosphorescence, reflection, diffraction and deflection resulting from the luminescence.

In an embodiment of the present invention, the source can be coupled to the detection volumes using a special adapter. The adapter simultaneously provides for coupling of fluorescent emissions from the samples to the detection system.

In an embodiment of the present invention, the excitation light and emission light can be separately coupled from the bottom, side, or top of any or all detection volumes as preferred.

In an embodiment of the present invention, the optical fibers used for transferring the excitation or emission can be made of glass, plastic, a confined liquid or any other type of light pipe. The coupling adapter can be made of glass, plastic, a confined liquid or any other suitable material.

In another embodiment of the present invention, two excitation transfer fibers and the lamp can be connected in a loop so that light can pass repeatedly around the loop until absorbed by the detection volume. In another embodiment the coupling adapter can contain reflective regions which reflect unused excitation light back into the relay fiber or which form a cavity so that unused light passes repeatedly through the detection volume.

In other embodiments of the present invention, the excitation or emission light can be coupled to fibers using small lenses with or without a larger relay or projection lens.

In other embodiments of the present invention, the specific geometry of the source, fibers, wells and detection elements can be changed to any practicable arrangement. Lenses used can consists of multiple elements, of both positive and negative power, and can contain glass and/or plastic elements. In alternative embodiments Fresnel lenses or a diffractive optics can be used.

In various embodiments of the present invention, the light from separate lamps can impinge on separate detection volumes or the light from one lamp can excite multiple detection volumes at once.

In an embodiment of the present invention, the number of samples illuminated can be varied by varying the number of lamps, which are active. The lamp can be activated during measurements and turned off at other times to minimize the heat generated.

In an embodiment of the present invention, each lamp contains a luminescent praseodymium doped YAG single crystal fiber or other doped single crystals or rod of the same diameter as the delivery fiber. In another embodiment each lamp contains a luminescent praseodymium doped glass fiber or rod of the same diameter as the delivery fiber. In another embodiment, each lamp contains a luminescent doped plastic optical fiber or rod of the same diameter as the delivery fiber. The fibers and rods can have a circular, square or rectangular cross section. Also, the fiber or pipe diameter can be smaller or larger than the delivery fiber and then optically coupled to the delivery fiber using for example a tapered cone.

In another embodiment of the present invention, some lamps can contain alternate materials to allow for the generation of other colors, including infrared and ultraviolet. In one embodiment, these lamps of alternate colors are connected in parallel so that different colors are imaged to different detection volumes. In another embodiment the alternate color lamps are connected in series so that the light of each color passes through the constituent light pipes of lamps of different colors so that each detection volume can be illuminated by light of one or more alternate colors at any given time. In another embodiment the lamp can contain one or more materials capable of producing luminescence at more that one wavelength. As an example, multiple rare earth metal atoms can be doped into a glass host and multiple organic emitters can be doped into a plastic host. In this embodiment, different pump sources such as different color LEDs can be turned on or off to cause the production of the different colors.

In other embodiments of the present invention, relay fibers can be used to direct different wavelengths of light on a detection volume at different positions thereby allowing simultaneous detection of different species present in the detection volume. These different excitation fibers can be positioned to allow detection of species at earlier or later times during the procession of the reaction. In this or other embodiments emission can be collected from more than one region of the detection volume.

In other embodiments of the present invention, the lamp can contain a luminescent fiber of larger or smaller diameter than the delivery fiber with provision for efficient coupling of the two.

In another embodiment of the present invention, the lamp can contain a larger diameter hollow fluorescent tube, which can be "necked down" in diameter to match the delivery fiber.

In another embodiment of the present invention, the lamp can contain a large fluorescent rod, which can be coupled to more than one delivery fiber.

In various embodiments of the present invention, the fibers, rods or tubes form light pipes that can be coated with one or more layers of luminescent material in thick or thin film form. Praseodymium or other rare earth doped lanthanum oxysulfides can be utilized as the film.

In another embodiment of the present invention, the lamp can contain a tube, which contains within it a luminescent material in powder, liquid or other form.

In various embodiments of the present invention, the luminescent light pipe can be of an appropriate cross sectional shape and can be free standing or constructed on a substrate.

Potential luminescent materials suitable for use in this invention include, but are not limited to, CRT or lamp phosphors including all of the lanthanides doped into lanthanum, yttrium, or gadolinium oxides or oxysulfides, or other phosphors with suitable emissions. One can easily generate a wide range of colors based on readily available and known phosphor chemistries. This wide range of colors matches the numerous widely accepted and commonly used fluorophors for bioanalytical applications. Other suitable materials include all of the lanthanides doped into a glass, an organic material containing one of the lanthanides, or a confined solution containing lanthanides.

In alternative embodiments of the present invention, the lamp can be switched on and off rapidly so that a time varying excitation can be produced. The color of the excitation can also be rapidly varied. These rapid variations in excitation can be used in conjunction with time-based detection to increase system sensitivity or to allow for the discrimination of differing numbers, types, or states of fluorescence targets.

Figure 2:
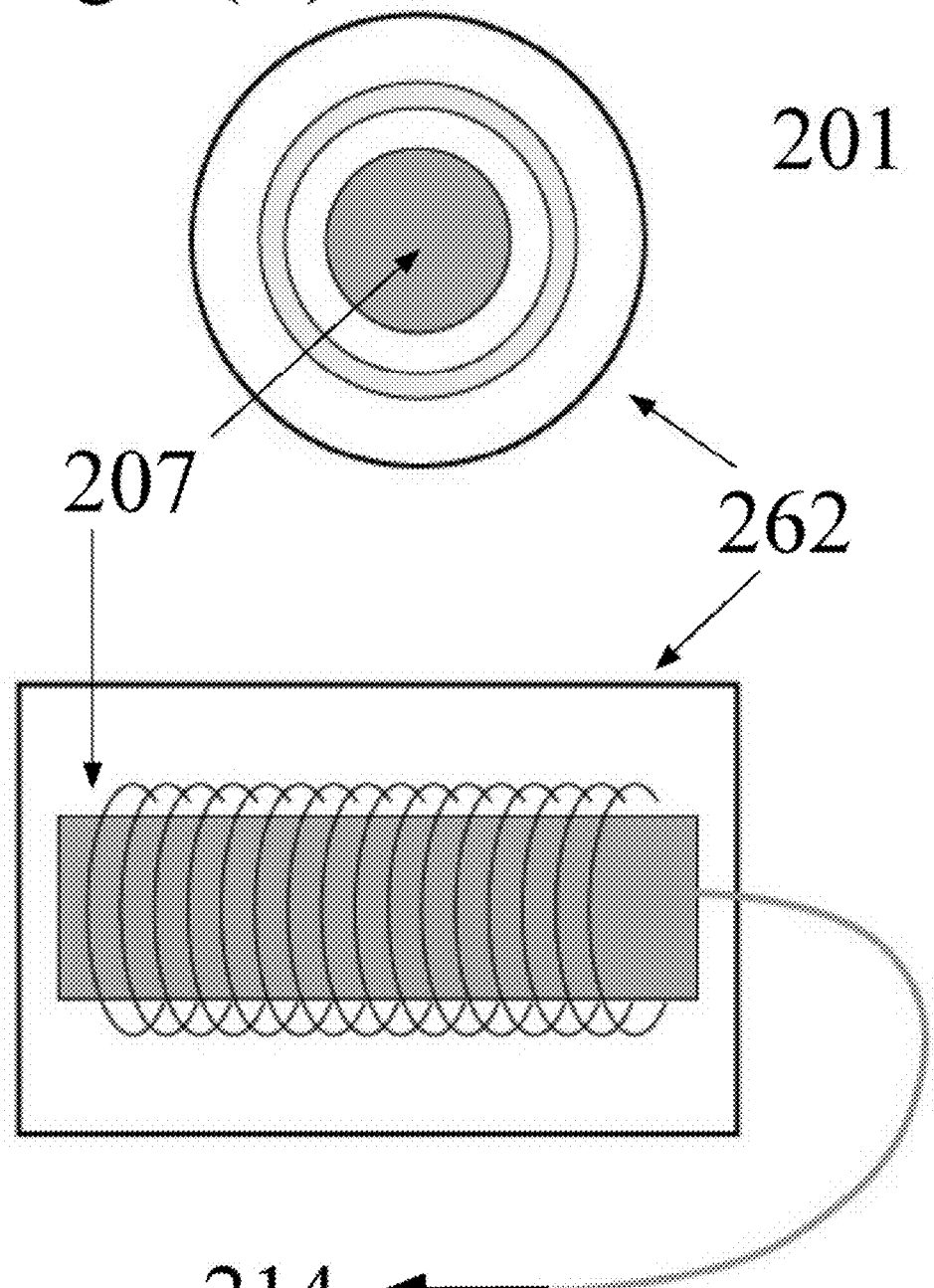
FIG. 2A shows a schematic drawing (of a luminescent pipe viewed end on) of an LED pumped lamp. The lamp can be based on a fiber coiled around a linear array of LEDs.
FIG. 2B shows a schematic drawing (of a luminescent pipe viewed side on) of a bar of LED's exciting a luminescent light pipe in the form of an optical fiber.

In an embodiment of the present invention, the luminescent fiber or fibers of praseodymium doped glass or doped plastic optical fiber are excited (pumped) by an array of LEDs with strong emission near 450 nm in wavelength as shown in FIG. 2. In alternative embodiments of the present invention, the pump source can be replaced with one or more similar devices such as other color LEDs, fluorescent lamps, semiconductor or solid-state lasers, arc lamps, or incandescent lamps.

Another lamp embodiment uses an outer waveguide to deliver pump energy to the luminescent pipe. The pipe can be located at the center of the outer or pump waveguide and LEDs are located at either end. The pump waveguide may be filled with a solid, liquid, or gas whose refractive index can be lower than the index of the luminescent pipe. The outer surface of the pump waveguide may be metalized to minimize losses. The luminescent pipe can be positioned in any orientation of the pipe. This orientation can be chosen to maximize the absorption of the excitation light inside the pipe. The luminescent material can be formed into any shape including fibers. More than one pipe emitting more than one pump wavelength can use the same pump waveguide. Different luminescent pipes can be excited by activating different excitation LEDs.

Another embodiment, which emits multiple colors when excited by a linear array of LEDs, is shown in FIG. 7. The pump energy can be delivered to the luminescent pipe using an elliptical cavity geometry. The luminescent pipe can be located at one focus and the excitation can be located at the other focus. This geometry also works for a single color pipe.

Figure 10:
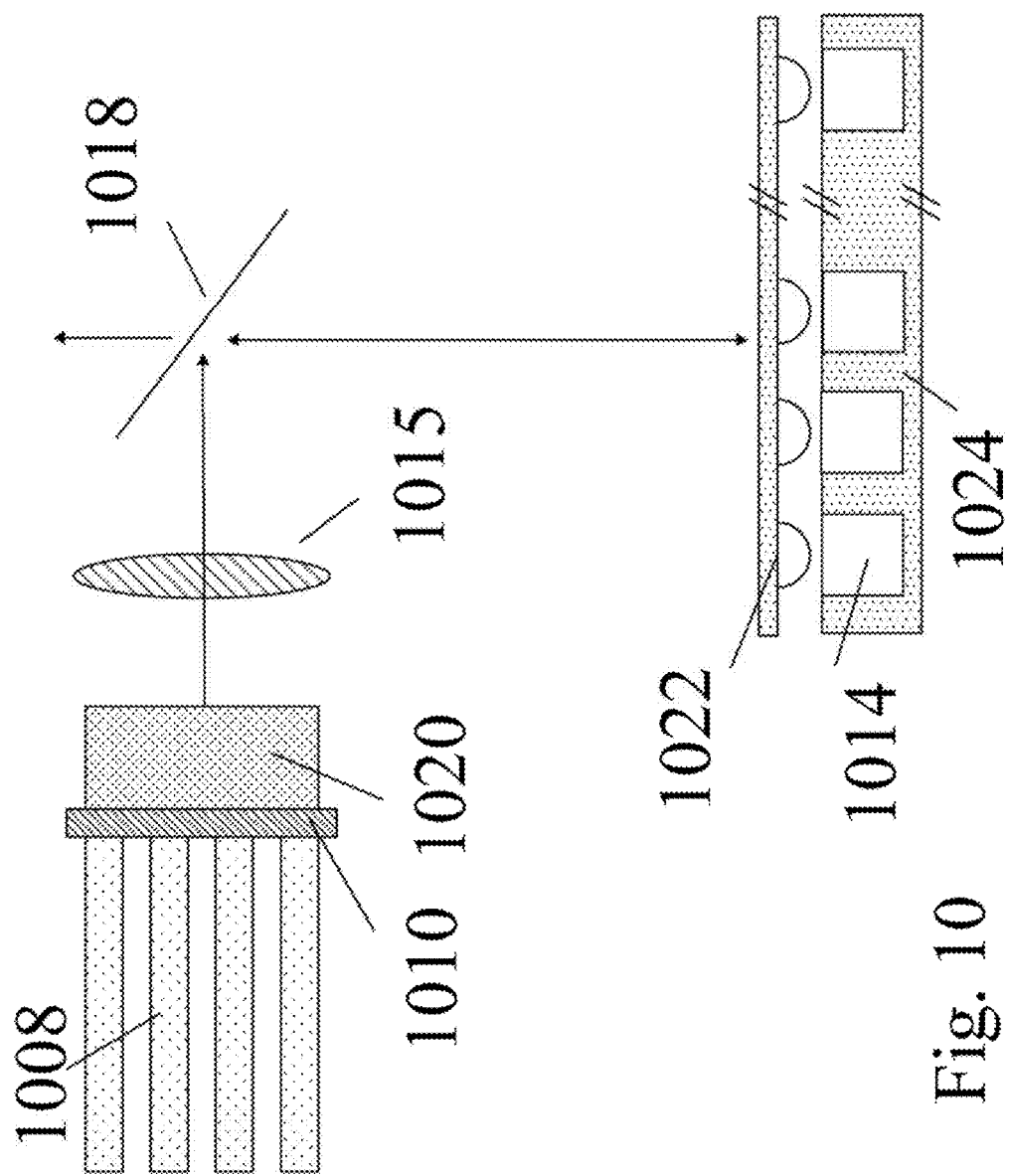
FIG. 10 shows a schematic drawing of a system with multiple luminescent light pipes. The excitation can be delivered to each well via a micro-lens array. The emission can be collected by the same lens array. The excitation and emission are separated using a dichroic beam splitter.

In another embodiment of the present invention, the excitation can be delivered to each detection volume via a microlens array as shown in FIG. 10. A plurality of lamps (1008) with filters (1010) for selecting the wavelength of choice, in conjunction with a device for coupling (1020) the lamps and magnifying the luminescence with a lens system (1015) and a dichroic beam splitter (1018) for transferring the excitation and emission light to the micro lens array adapter (1022), for coupling luminescence into the wells (1014) in the microtiter plate (1024). The emission can be collected by the same lens array. The excitation and emission can be separated using the dichroic beam splitter (1018).

Figure 11:
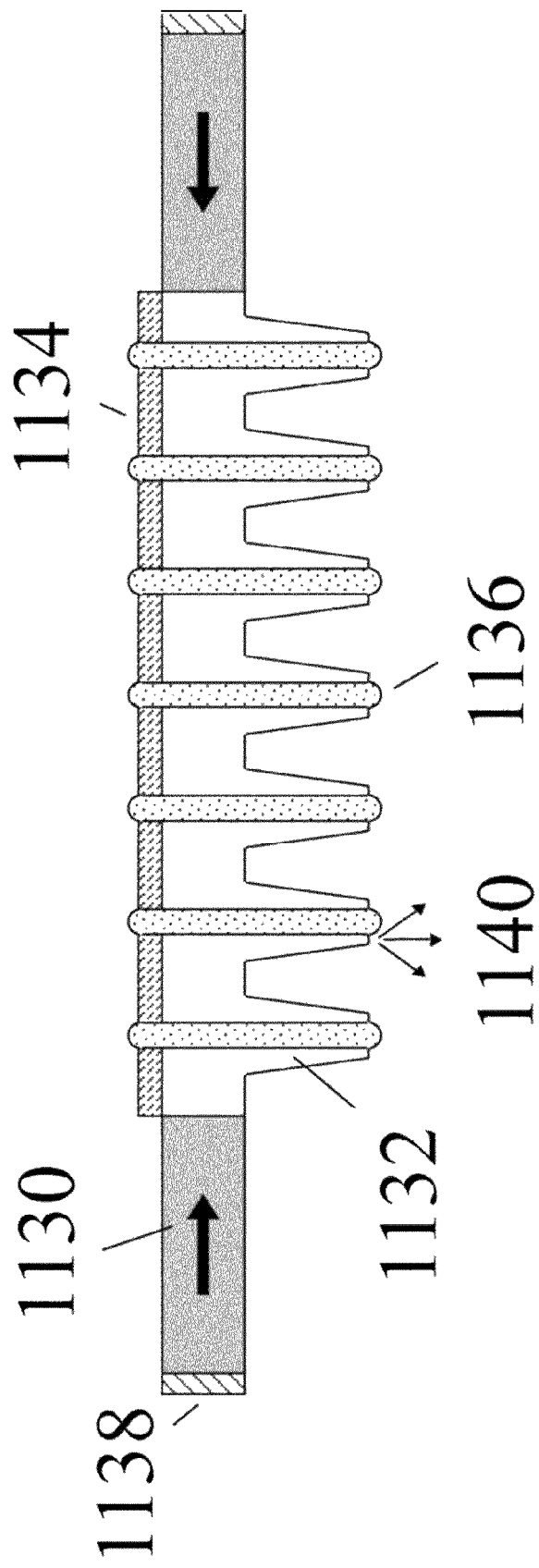
FIG. 11 shows a schematic drawing of a compound integrated optical array. The excitation and emission are delivered to each well via a conical protrusion into each well. This protrusion consists of a central pipe surrounded by a conical external section. The central pipe can have an index that can be lower than the surrounding area and can be hollow. Excitation can be delivered to each well via the conical section while emission can be collected by the central pipe.

In another embodiment of the present invention, the excitation light can enter a single coupling plate which can be designed to distribute light to the individual detection volumes for analysis while simultaneously collecting emitted light for detection as shown in FIG. 11. In this embodiment, excitation can be delivered from the luminescent light pipe (1130) to each detection volume and can be collected from each detection volume using a conical protrusion into each detection volume. This protrusion consists of a central pipe (1134) surrounded by a conical external section. The central pipe can have an index that can be lower than the surrounding area and can be hollow and coated with a reflective layer. Excitation can be delivered to each detection volume via the conical section while emission can be collected in the central pipe. A mirror (1138) can be used to increase the luminescence in the light pipe. This device couples light into a microtiter plate and collects the emission (not shown). The analyte in each detection volume delivers the excitation light to each well (not shown). The emission from each well can be collected in a central light pipe (1136) and transmitted normal to the surface above the central light pipe (1136). The excitation light (1140) is delivered through a conical protrusion (1132) into each detection volume. The luminescence from each detection volume is collected by a central light pipe (1136) and directed towards the detector. A scattering or reflective surface (1134) is used to homogenizes the light distribution across the microtiter plate.

In other embodiments of the present invention, more than one coupling plate can be used with each plate coupled to a subset of the complete array of detection volumes. These multiple coupling plates can be connected to one excitation source or can be connected to distinct sources. The coupling plate(s) can be made of glass, plastic, a confined liquid or any other suitable material. In an embodiment of the present invention, the plate(s) can provide uniform luminescence to each detection volume, uniformly collect the emission and minimize the emission crosstalk. Excitation uniformity can be increased by applying a surface treatment to the upper surface of the coupling plate. Improved imaging of the emission can be obtained by providing a lens element on the top side of the central section.

Figure 12:
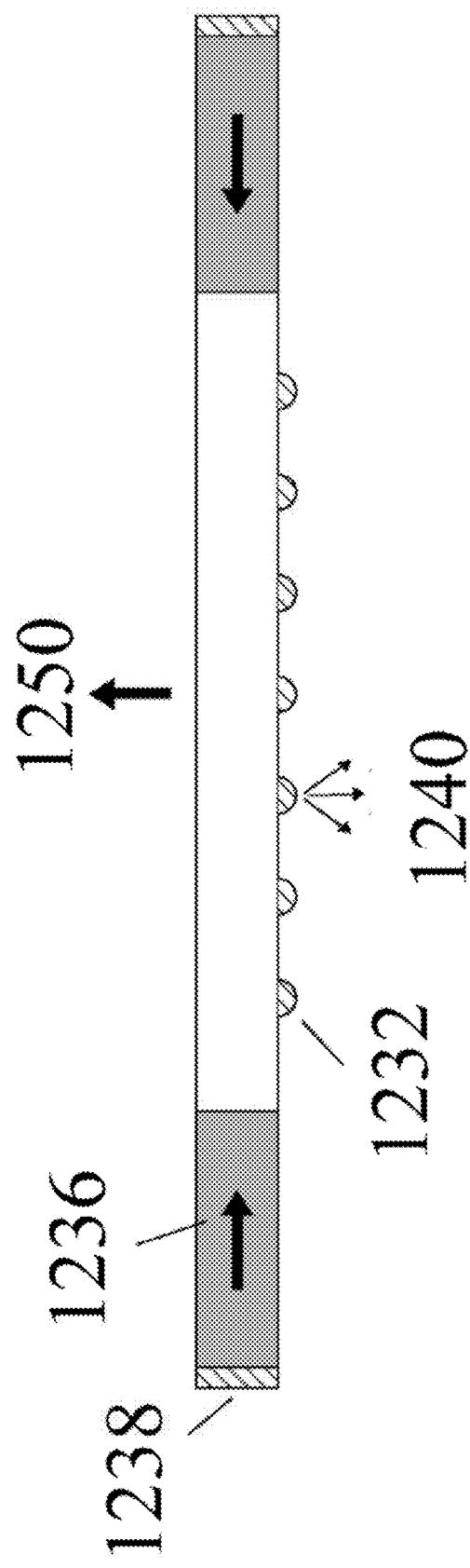
FIG. 12 shows a schematic drawing an integrated optical array consisting of a transparent coupling plate with "dimples", hemispheres or other surface modifications which cause light to leave the light pipe and enter each well. The dimples are designed to represent a small fraction of the transparent window above each well.

In another embodiment of the present invention shown in FIG. 12, a transparent coupling plate can be utilized which consists of a light pipe (1236) with mirror (1238) and "dimples", hemispheres or other surface modifications (1232) which cause the light to leave the light pipe and enter each detection volume. The dimples are designed to represent a small fraction of the transparent window above each detection volume. In this manner, the emission (1240) is most likely going to be transmitted through the plate without scattering and transferred to the detector (1250). The dimples can be designed so that they provide uniform luminescence to the detection volumes and minimize emission crosstalk between the detection volumes. The dimples can be in the shape of a retro-reflector so that light that is not transmitted can be reflected back into the waveguide. In this embodiment emitted light can be collected by a lens or system of lenses which image through the coupling plate. In other embodiments more than one coupling plate can be used with each plate coupling to a subset of the complete array of detection volumes. These multiple coupling plates can be connected to one excitation source or can be connected to distinct sources. The coupling plate(s) can be made of glass, plastic, a confined liquid or any other suitable material. The emission (1240) is shown leaving the pipe to enter the sample volume. The microtiter plate and the fluorescence are not shown.

Figure 13A:
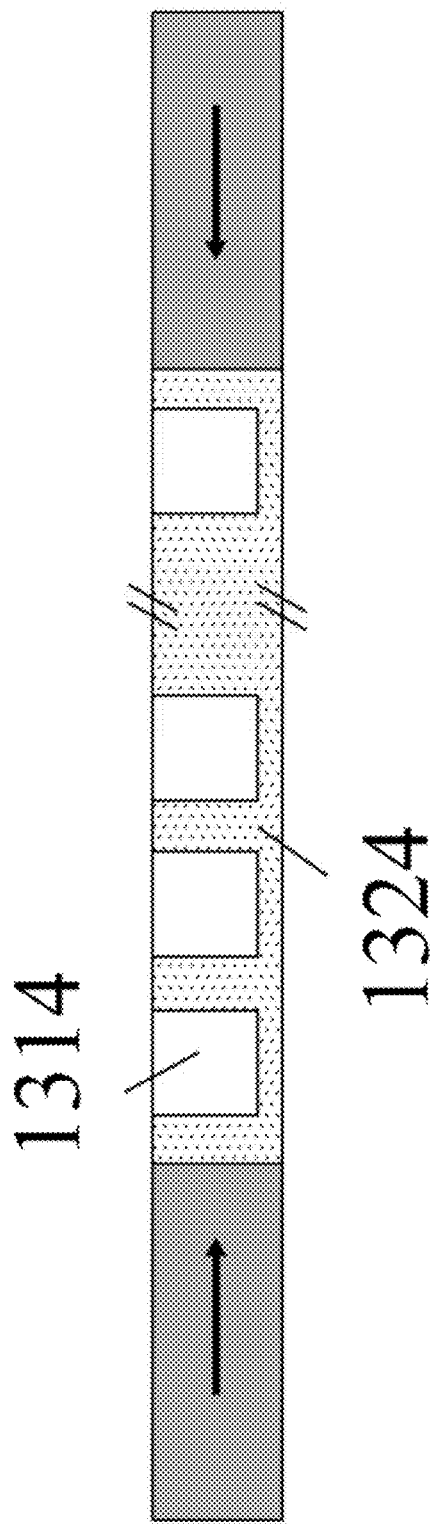
FIGS. 13A and B shows side view and top view respectively of schematic drawings of a transparent micro-titer plate excited by one or more luminescent light pipes. The plate serves as both a micro-titer plate and a coupling plate. The plate can consist of a series of internal light pipes connecting subsets of wells (the schematic illustrates four parallel sections)
Figure 13B:
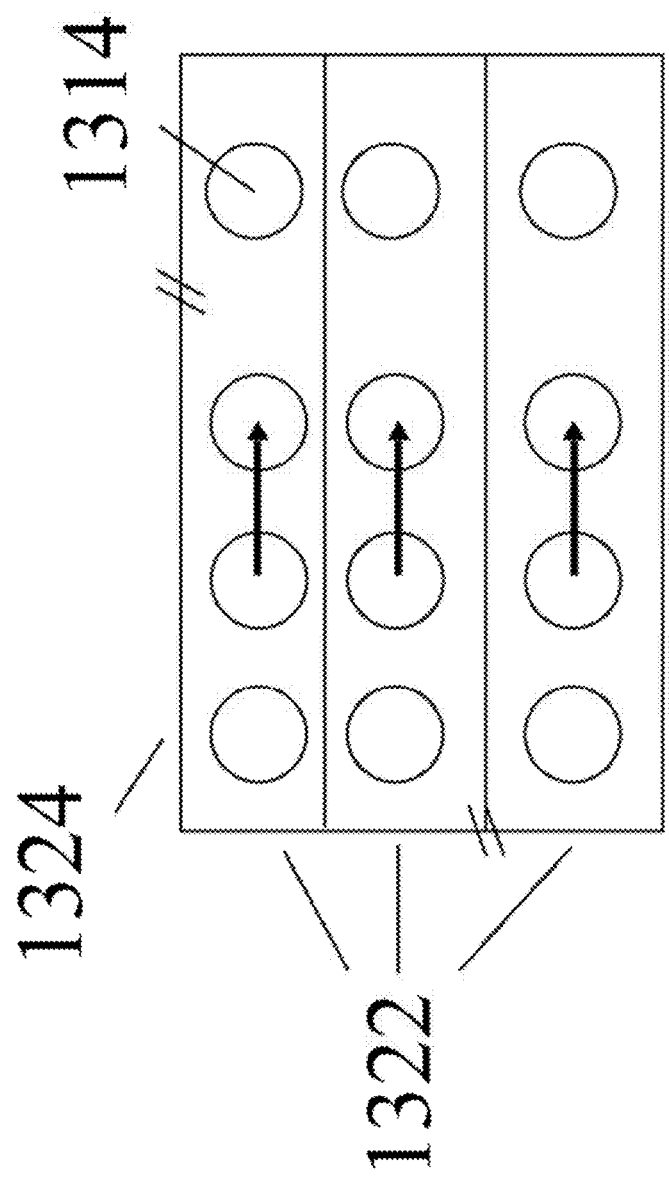

In another embodiment of the present invention shown in FIGS. 13A and B, a completely or partially transparent coupling plate (1324) can function to define the detection volumes (1314) containing the analyte. The coupling plate can consist of a series of internal light pipes (1322) connecting subsets of detection volumes. The various internal light pipes can be separated by opaque walls. This internal structure can be designed to provide uniform intensity to each detection volume and minimize emission crosstalk between the detection volumes. In this embodiment emitted light can be collected by a lens or system of lenses which image the coupling plate or fibers can be used to collect light from each detection volume. In other embodiments, more than one coupling plate can be used with each plate coupling to a subset of the complete array of detection volumes. These multiple coupling plates can be connected to one excitation source or can be connected to distinct sources. The coupling plate(s) can be made of glass, plastic, a confined liquid or any other suitable material.

Figure 15:
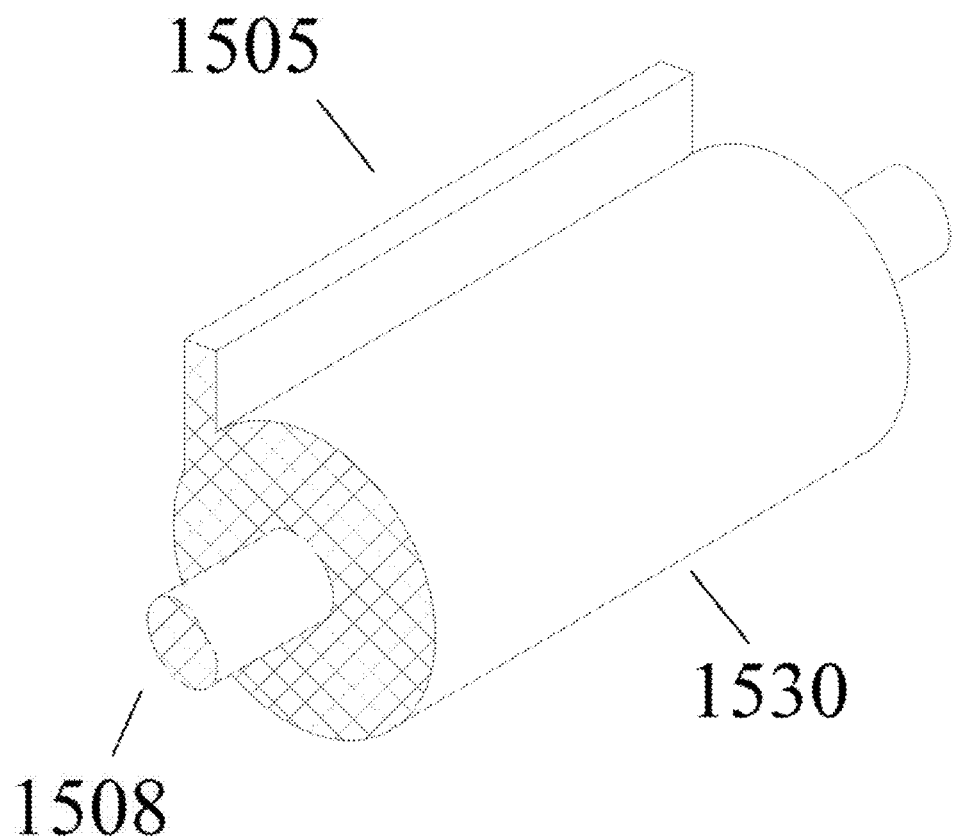
FIG. 15 shows a schematic drawing of a light pipe encased by a cylindrical chamber which feeds off a linear LED array.

In another embodiment of the invention shown in FIG. 15, a linear array of LEDs (1505) can be mounted on the external side of a cylinder. The light can be injected into the cylindrical chamber (1530) which contains the luminescence light pipe (1508). The inside cylinder walls are highly reflective and, as an example, could be coated with Oerlikon Silflex. This design maximizes the amount of reflective surface surrounding the light pipe. The pipe can be located at any location an orientation within the cylinder to maximize the amount of LED light that can be absorbed.

In other embodiments of the present invention, some of the light sources can emit infrared light and be used to heat detection volumes as part of the analysis process.

Figure 1:
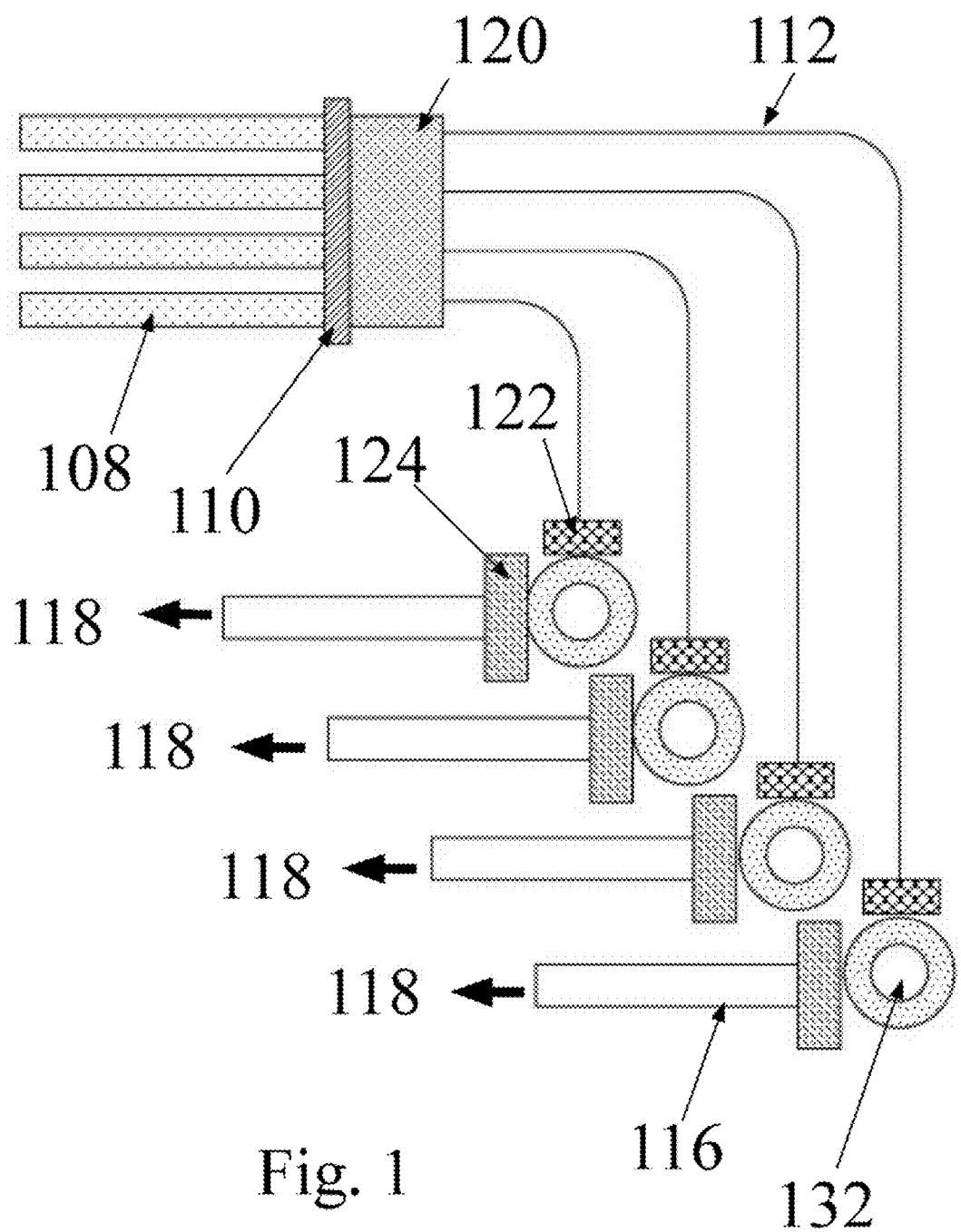
FIG. 1 shows a schematic drawing of system with multiple luminescent light pipes connected to optical fibers which interface with capillaries through fiber capillary adapters and fluorescence collection optics.
Figure 3:
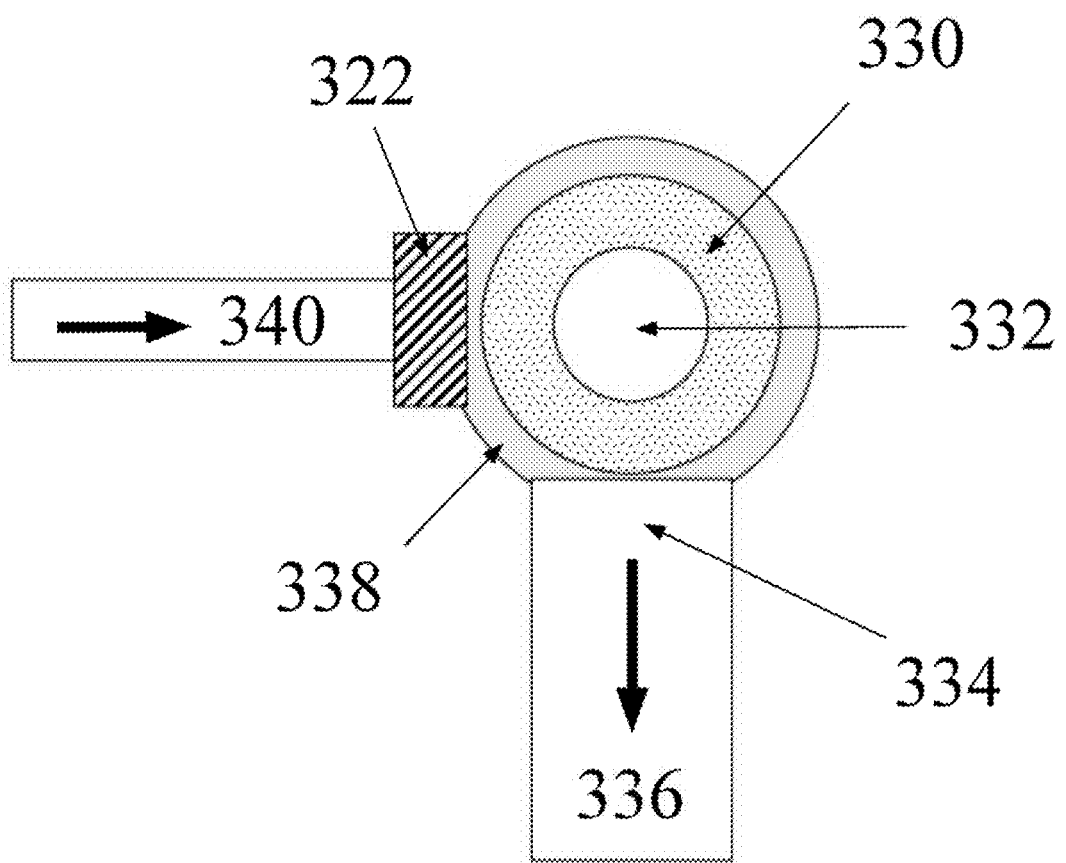
FIG. 3 shows a schematic drawing (of a capillary viewed end on) illustrating the interface between the fiber optics and the capillaries.

As shown in FIG. 1, in an embodiment of the present invention, a plurality of lamps (108) with filters (110) for selecting the wavelength of choice, in conjunction with a device for coupling (120) the lamps into multiple optical fibers (112), multiple optical fibers for transferring the excitation light to the capillaries (132) (note 132 points to the bore of the capillary), adapters for coupling light from the fibers into the capillaries (122) and for coupling fluorescence from the capillaries into collection fibers (124) and collection fibers (116) for transferring the emitted light (118) to a detector array (not shown). In an embodiment of the present invention, fibers for coupling fluorescence from the capillaries can be placed at 90° to the excitation fibers (as shown in FIG. 3).

In an embodiment of the present invention, a luminescent light pipe can consist of a pipe coupled to a transparent fiber. In an embodiment of the present invention, a luminescent pipe can be a continuous fiber, which can directly deliver the luminescence to one or more capillaries or be coupled to a transparent fiber. In an embodiment of the present invention, a luminescent pipe can consist of a luminescent rod.

In an embodiment of the present invention, a coupling optic can contain a filter to narrow excitation spectrum.

In an embodiment of the present invention, the coupling adapter can contain reflective surfaces, which reflect light passing through the capillary back into the capillary. These reflecting surfaces may form a ring cavity or other form of cavity with the result that excitation light passes repeatedly through the flow region of the capillary. In an embodiment of the present invention, the reflective surfaces are designed to enhance both the excitation and emission intensity. In an embodiment of the present invention, the width of a reflective ring can be 1.5 times the diameter of the capillary. In an embodiment of the present invention, the width of a reflective ring can be 1.5 times the spot size. In an embodiment of the present invention, the reflective ring can be 60 microns-100 microns in width. In an embodiment of the invention the spot size can be 40-60 microns.

In an embodiment of the present invention, one or more LED's (207) in parallel are used as a lamp source (see FIG. 2A which shows a luminescent pipe (201) viewed end on and FIG. 2B which shows a luminescent pipe viewed side on) mounted inside a housing (262) directing the light towards the sample (214). In this example, the luminescent light pipe can be a continuous fiber wrapped around a linear array of LEDs. In various embodiments of the present invention the length of the luminescent pipe can be extended and the number of LED's in parallel increased in order to increase the intensity of the luminescent pipe. LED's have a number of advantages for incorporation into a luminescent pipe including their engineering simplicity, long life, low manufacturing cost, flexible emission wavelengths and high light output power. In an embodiment of the present invention, more than one luminescent pipe can be excited by the same LED source. In an embodiment of the present invention, a luminescent pipe can generate more than one color.

In an embodiment of the present invention, a source can be coupled to the capillaries using a special adapter assembly for coupling this light into the capillary system. In an embodiment of the present invention, an adapter assembly can also simultaneously provide for coupling of fluorescent emissions from the samples to the detection system.

In various embodiments of the present invention, optical fibers used for transferring the excitation or emission can be made of glass, plastic, a confined liquid or any other type of light pipe. In various embodiments of the present invention, a coupling adapter can be made of glass, plastic or any other suitable material.

In various embodiments of the present invention, a capillary can be used as a light pipe for transferring either the excitation or emission light to or from the active region.

In an embodiment of the present invention, two excitation transfer fibers and the lamp can be connected in a loop so that light can pass repeatedly around the loop until absorbed by the capillary. In an embodiment of the present invention, a coupling adapter can be designed to collimate the excitation light so that it can pass from the fiber on one side of the capillary to be easily collected by the fiber on the opposite side of the capillary. In an embodiment of the present invention, the coupling adapter can contain reflective regions, which reflect unused excitation light back into the relay fiber. In an embodiment of the present invention, the coupling adapter can contain reflective regions, which form a cavity so that unused light passes repeatedly through the flow region of the capillary.

Figure 5:
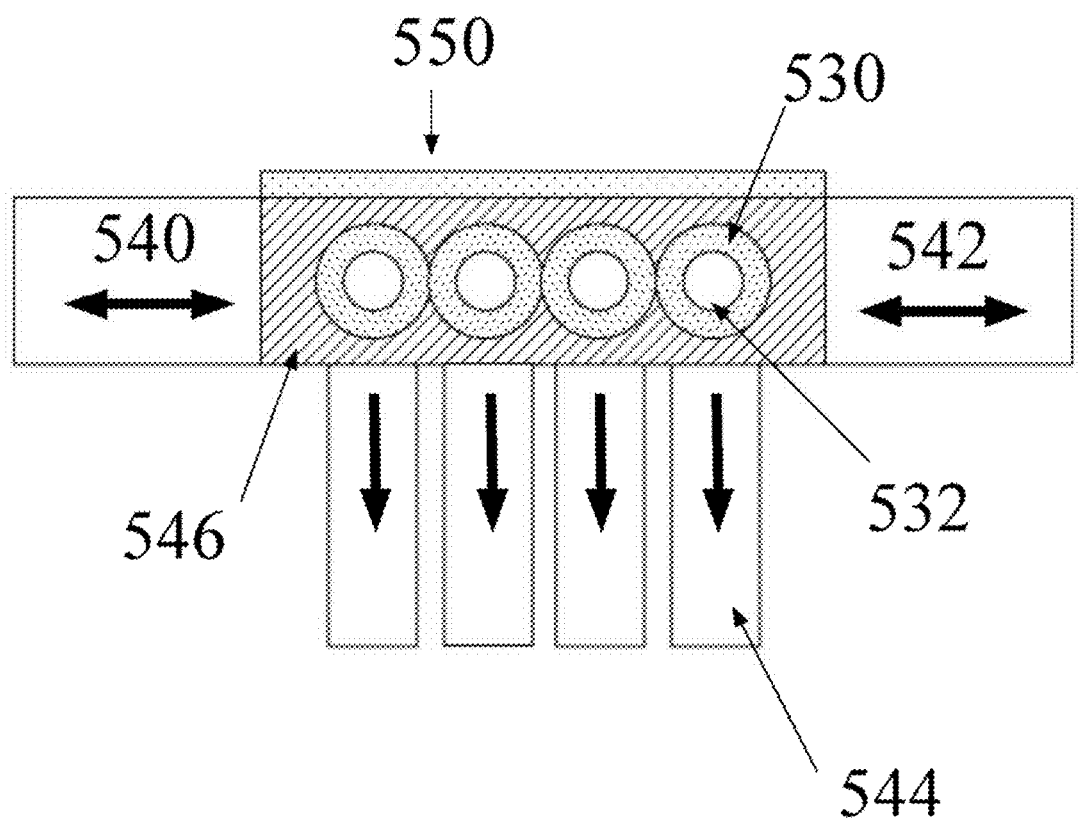
FIG. 5 shows a schematic drawing (of a capillary viewed end on) illustrating the interface between a one-dimensional array of capillaries from two optical fibers mated perpendicular to the entire array. The light can be coupled from each fiber to the capillary array via a light pipe adapter. In this manner, the same excitation light travels perpendicular through all the capillaries.

In another embodiment of the present invention, as seen in FIG. 5, a light pipe adapter can function as an extension of the excitation transfer fiber or light pipe causing light to impinge on more than one capillary (532) (note 532 points to the bore of the capillary) from the side. In this embodiment, one of the ends of light pipe adaptor can serve as a retro reflector to increase the intensity in the capillaries.

In another such embodiment of the present invention, light enters from both ends (540 and 542) of the adapter. In this embodiment of the present invention one or more optical fibers deliver excitation from one or more luminescent pipes to the capillary light pipe adapter from two directions. Light propagates through the adapter and out the opposite fiber. Light can travel back around through one or more luminescent pipes and re-enter the capillaries. The light pipe adapter can be designed to efficiently pipe the light from one end of the pipe to the other.

In various embodiments of the present invention, the light pipe adapter functions to relay the light to any number of capillaries and through multiple reflections to make the luminescence uniform. Therefore, the light (540) piped by the adapter (546) can be transferred to multiple capillaries with great uniformity.

In an embodiment of the present invention, an adapter (546) can be sufficiently wide so that the capillaries fill region that is smaller than the adapter. In another embodiment of the present invention, a light pipe adapter can be narrower than the capillaries. In this case, the light pipe adapter acts as a bridge to carry light from one capillary to the next capillary.

In various embodiments of the present invention, a light pipe adapter can have its surface treated (550) to internally reflect light directly into the multiple flow regions. This treatment can consist of mechanical grooves, holographic patterning and thin film multi-layer dielectrics. This treatment can be made to be wavelength selective allowing the fluorescence emission from the capillaries to preferentially leave the light pipe adaptor at a specific angle. Such treatments are particularly useful when achieving uniformity over a relatively few number of capillaries.

In an embodiment of the present invention, emission can be collected by fibers mated to each capillary. The collection fiber (544) leads to the detector (not shown) in FIG. 5.

In an embodiment of the present invention, the coupling adapter can be made of material which can be index matched to the capillary body, causing the capillary body to function as part of the adapter. In another embodiment of the invention, material of the adapter can be index matched to the flowing liquid inside the capillary. In another embodiment of the present invention, an adapter can replace the capillaries with the flow proceeding through the adapter. In another embodiment, the adapter can consist of a hollow structure filled with an index matching fluid matched to the capillary body or flowing fluid. The adapter can be made using standard etching technologies.

In another embodiment, the light pipe adapter can be used with other light sources including edge emitting LEDs and lasers.

In various embodiments of the present invention, the excitation (340) or emission (336) light can be coupled to fibers with or without a larger relay or projection lens. One example is shown in FIG. 3. In an embodiment of the present invention, a collection fiber (334) may be used to collect the emission light (336) from one or more capillaries (332) (note 332 points to the bore of the capillary) directly to a detector or an array of detectors. With the exception of the coupling optic (322), the capillary surface (330) can be surrounded by the ring reflector (338).

Figure 4:
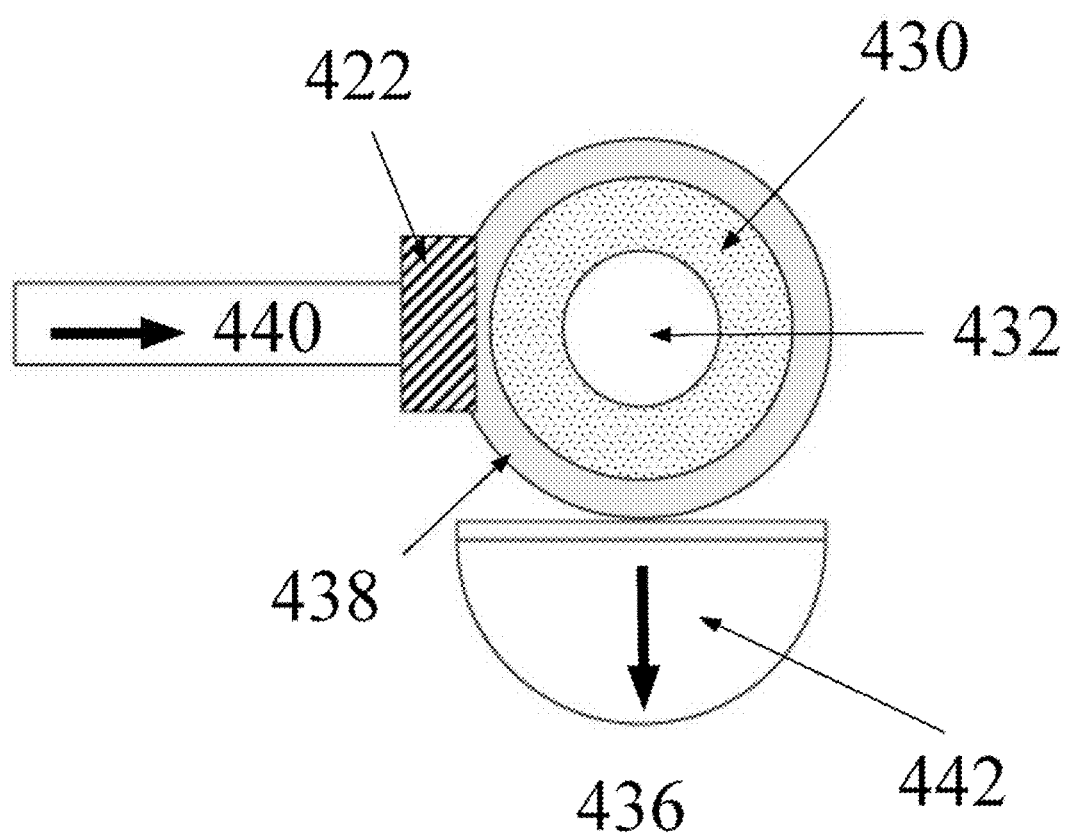
FIG. 4 shows a schematic drawing (of a capillary viewed end on) illustrating the interface between the fiber optics and the micro lens optical element and the capillaries.

In various embodiments of the present invention, the excitation (440) or emission (436) light can be coupled to fibers using small lenses with or without a larger relay or projection lens. One example is shown in FIG. 4. In an embodiment of the present invention, a lens (442) may be used to image the emission light (436) from one or more capillaries (432) (note 432 points to the bore of the capillary) directly to a detector or an array of detectors. With the exception of the coupling optic (422), the capillary surface (430) can be surrounded by the ring reflector (438).

In various embodiments of the present invention, the specific geometry of the source, fibers, capillaries and detection elements can be changed to any practicable arrangement. In various embodiments of the present invention, lenses used can consist of multiple elements, of both positive and negative power, and can contain glass and/or plastic elements. In an embodiment of the present invention, Fresnel lenses can be used. In an embodiment of the present invention, diffractive optics can be used.

In an embodiment of the present invention, the light from separate lamps can impinge on separate capillaries. In an embodiment of the present invention, the light from one lamp can excite multiple capillaries. In an embodiment of the present invention, the light from one lamp can simultaneously excite multiple capillaries.

In an embodiment of the present invention, the number of samples illuminated can be varied by varying the number of lamps, which are active. In an embodiment of the present invention, a lamp will be activated during measurements and turned off at other times to minimize the heat generated.

In an embodiment of the present invention, rare earth activated glass can be used as light pipes. In one embodiment of the invention Terbium (Tb) is used to dope the glass rods used as a light pipe. In another embodiment of the invention, Praseodymium (Pr) is used to dope the glass rods used as a light pipe. Table 1 gives a list of some common rare-earth-dopants in the UV spectra and the examples of emission wavelength ranges.

Figures 6A, 6B:
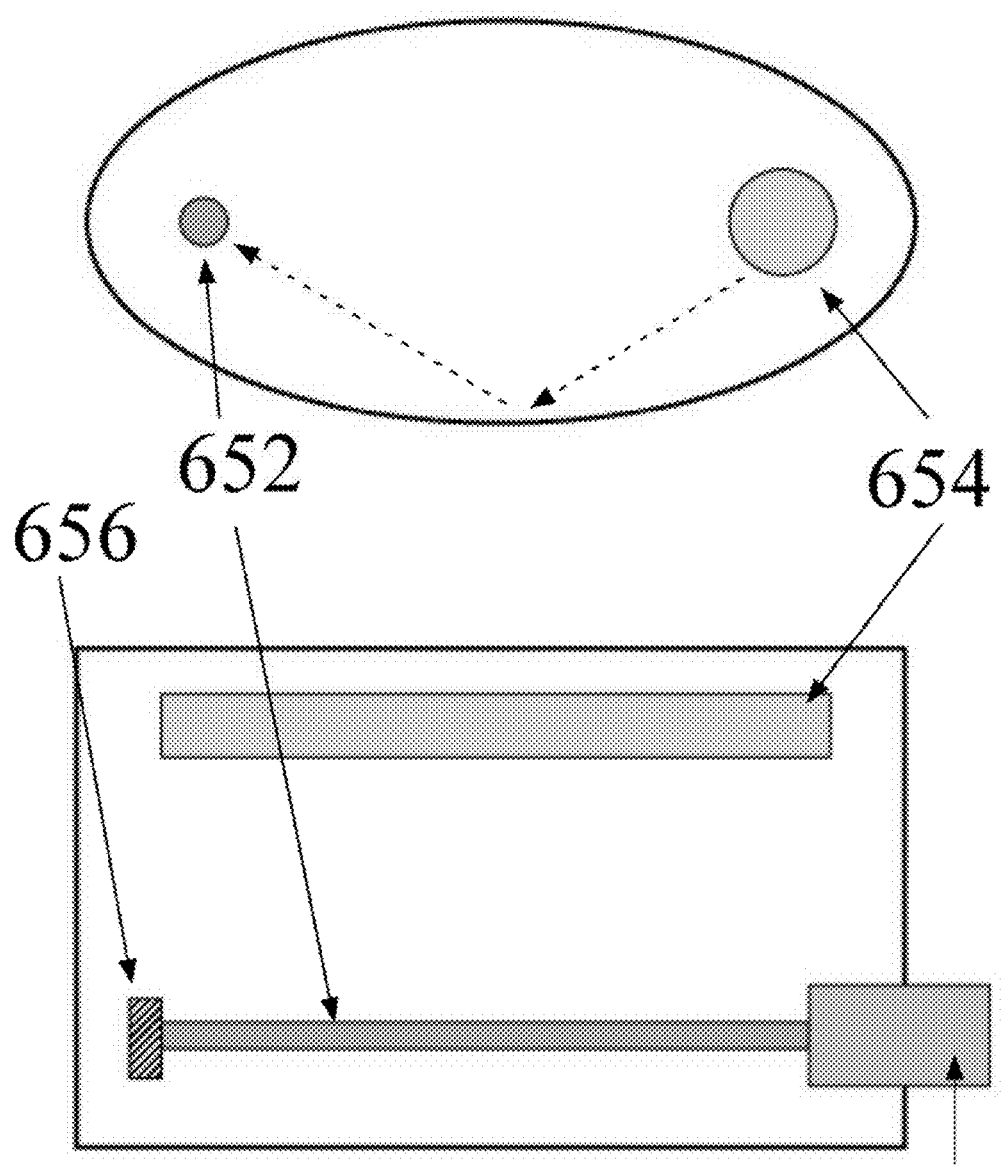
FIG. 6A shows a schematic drawing (side view) illustrating an elliptical reflector with a luminescent light pipe positioned at one focus of an elliptical reflector and a UV lamp located at the other focus.
FIG. 6B shows a schematic drawing (top view) illustrating an elliptical reflector with a luminescent light pipe positioned at one focus of an elliptical reflector and a UV lamp located at the other focus.

In an embodiment of the present invention, a lamp can contain alternate materials to allow for the generation of other colors, including infrared and ultraviolet. FIG. 6 shows a luminescent pipe (652) positioned at one of the two foci of an elliptical cavity with one light source (654) positioned at the other focus. This light source can be a UV lamp used to excite the light pipe. A back mirror (656) and coupling optic (652) are shown in FIG. 6. The coupling optic is shown as 658. FIG. 7 shows a luminescent pipe (752) positioned at one focus of an elliptical cavity with a linear array of LED's (754) positioned at the other focus. A back mirror (756) and coupling optic (752) are also shown in FIG. 7. The coupling optic is shown as 758.

TABLE 1

List of common rare-earth-dopants, their hosts and examples of emission wavelength ranges.

| Rare Earth Dopant | Common host glasses | Important emission wavelengths (nm) |
|---|---|---|
| Neodymium (Nd) | silica, phosphate glass | 1030-1100, 900-950, 1320-1350 |
| ytterbium (Yb) | Silica | 1000-1100 |
| erbium (Er) | silica, phosphate glass, fluoride glasses | 1500-1600, 2700, 550 |
| thulium (Tm) | silica, fluoride glasses | 1700-2100, 1450-1530, 480, 800 |
| praseodymium (Pr) | silica, fluoride glasses | 1300, 635, 600, 520, 490 |
| terbium (Tb) | Silica | 489, 547, 589, 622 |
| europium (Eu) | Silica | 610 |
| holmium (Ho) | Silica | 2100 |

Figure 8:
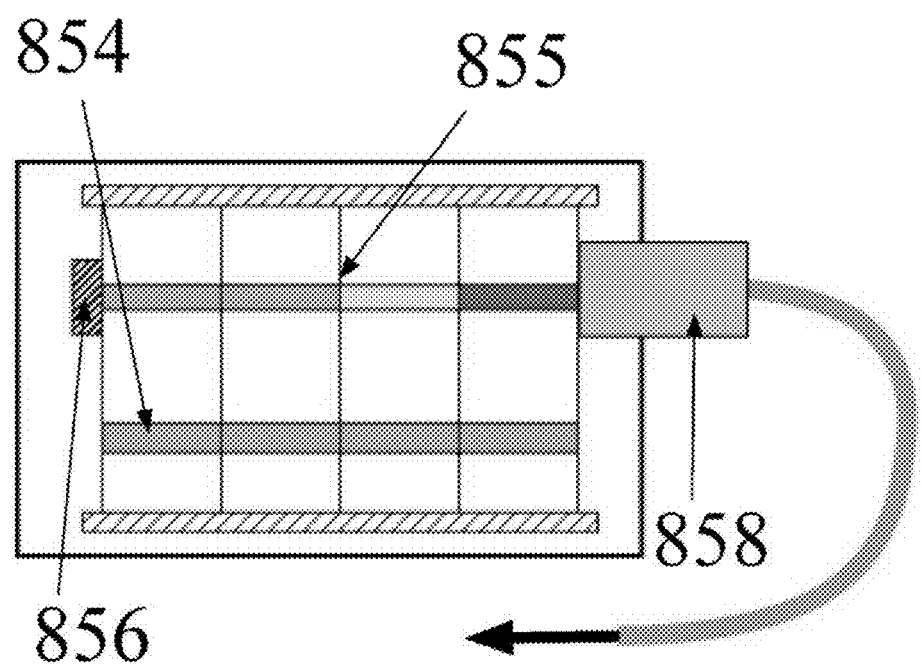
FIG. 8 shows a schematic drawing (top view) illustrating an elliptical reflector with a multi color luminescent light pipe positioned at one focus and a linear array of LED's positioned at the other focus of the ellipse.

FIG. 8 shows a multi color luminescent pipe (855) positioned at one focus of an elliptical cavity with a linear array of LED's (854) positioned at the other focus. A back mirror (856) and coupling optic (858) are also shown in FIG. 8. In an embodiment of the present invention, lamps of alternate colors are connected in parallel so that different colors are delivered to different capillaries. In an embodiment of the present invention, alternate color lamps are connected in series so that the light of each color passes through the constituent light pipes of lamps of different colors so that each capillary can be illuminated by light of one or more alternate colors at any given time. In an embodiment of the present invention, lamp can contain one or more materials capable of producing luminescence at more that one wavelength. In an embodiment of the present invention, different pump sources such as different color LEDs can be turned on or off to cause the production of the different colors.

Figure 14:
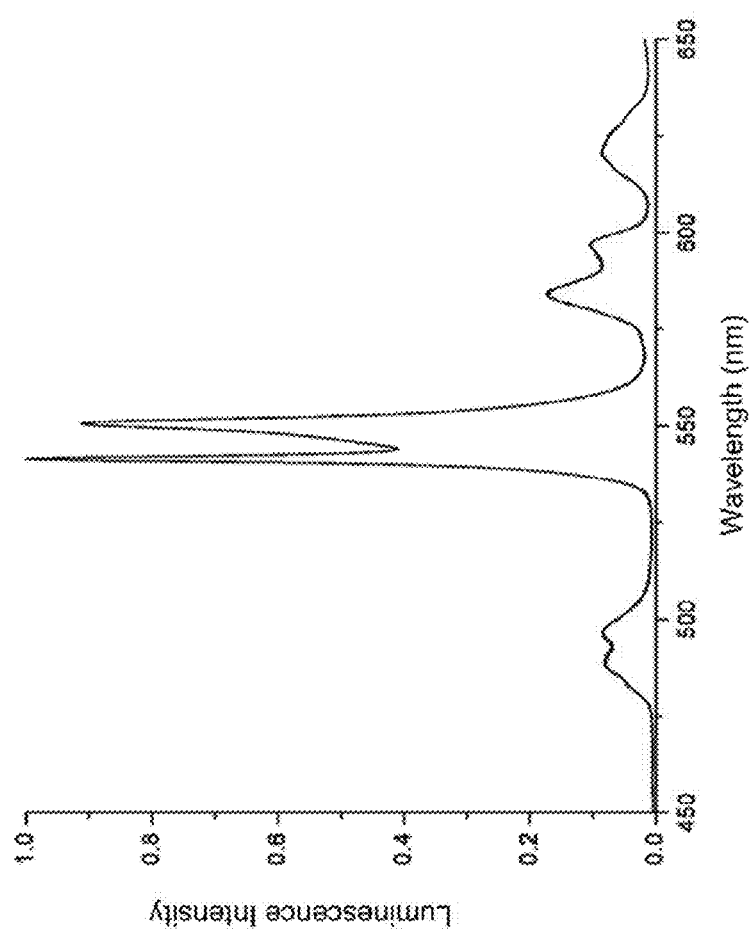
FIG. 14 shows the luminescence emission of a Terbium doped glass prototype when excited by UV light.

A was constructed in which a Tb doped glass rod was the luminescent pipe. The Tb glass rod was surrounded with five GE® Germicidal lamps (model G8T5, which each emit 2.1 W of UV light) positioned equidistant around the luminescent pipe. These UV lamps emitted radiation at a wavelength of 254 nm. At this wavelength, these lamps were germicidal (an agent that is destructive to pathogenic micro-organisms). The output of the light source subsystem containing the Tb doped glass light pipe is shown in FIG. 14 where an intense fluorescence emission is observed around 550 nm with a total power of 400 mW (the linewidth at 550 nm was 12 nm and the power was 240 mW). In the prototype, the Tb doped glass fluorescence produces an intense green beam of light which can be connected using a fiber optic tube to the capillary electrophoresis experiment. After one UV lamp is turned on, the fluorescence emission is observed. The fluorescence emission can be incrementally increased as the remaining four UV lamps are successively turned on producing 10.5 W of UV light. The fluorescence emission can be directed through the capillaries and the wavelength can be absorbed by molecules derivatized with the Cy-3 fluorophore from Invitrogen™. Other wavelengths of light can be generated using rare earth doped glass to detect other fluorophores conjugated with biological molecules of interest. Table 2 includes a list of some common fluorophores and the absorption and emission maxima.

In an alternative embodiment of the invention, a Tb doped glass can be chosen as the luminescent pipe with five LED's positioned equidistant around the luminescent pipe. In an alternative embodiment of the invention, a Tb doped glass can be chosen as the luminescent pipe positioned at one focus of an elliptical cavity with a bar of LED's positioned at the other focus. In an alternative embodiment of the invention, a Pr doped glass can be chosen as the luminescent pipe with five LED's positioned equidistant around the luminescent pipe. In an alternative embodiment of the invention, a Pr doped glass can be chosen as the luminescent pipe positioned at one focus of an elliptical cavity with a bar of LED's positioned at the other focus.

In an embodiment of the present invention, one or more optical fibers connected to one or more capillaries through one or more coupling optics connect with the capillaries at one or more locations in space. In an embodiment of the present invention, a species flowing through a capillary can be first excited at one location and the absorption or second excitation resulting from the first excitation can be measured at a second location. In an embodiment of the present invention, differences in the absorbed or emitted light with respect to space can be detected. In an embodiment of the present invention, differences in the absorbed or emitted light with respect to time can be detected. In an embodiment of the present invention, differences in the absorbed or emitted light with respect to frequency can be detected.

TABLE 2

List of some exemplary fluorophores and their absorption and emission maxima.

| | Absorption Maximum (nm) | Emission Maximum (nm) |
|---|---|---|
| Methoxycoumarin | 340 | 405 |
| Coumarins | 355 | 445 |
| Fluorescein | 494 | 518 |
| Bodipy-Fl | 505 | 513 |
| Ethidium Bromide | 518 | 605 |
| Bodipy-R6G | 528 | 550 |
| Rhodamine | 540 | 570 |
| TAMRA | 542 | 568 |
| Cy-3 | 550 | 570 |
| Tetramethylrhodamine | 555 | 580 |
| Bodipy | 565 | 571 |
| ROX | 574 | 602 |
| X-rhodamine | 580 | 605 |
| Texas Red | 590 | 610 |
| Naphthofluorescein | 605 | 675 |
| YOYO-3 | 612 | 631 |
| Cy-5 | 649 | 670 |

In an embodiment of the present invention, relay fibers can be used to direct different wavelengths of light on a capillary at different positions thereby allowing simultaneous detection of different species present in the flow stream of a capillary. These different excitation fibers can be positioned to allow detection of species at earlier or later times of elution from a capillary. In an embodiment of the present invention, emission can be collected from more than one region of a capillary.

In an embodiment of the present invention, a lamp can contain a luminescent fiber of larger or smaller diameter than a delivery fiber with provision for efficient coupling of the two fibers.

In an embodiment of the present invention, a lamp can contain a larger diameter hollow fluorescent tube, which can be "necked down" in diameter to match a delivery fiber.

In an embodiment of the present invention, a lamp can contain a large fluorescent rod, which can be coupled to more than one delivery fiber.

In an embodiment of the present invention, the fibers, rods or tubes form light pipes are coated with one or more thick layers of luminescent material. In an embodiment of the present invention, the fibers, rods or tubes form light pipes are coated with one or more thin layers of luminescent material. In an embodiment of the present invention, the fibers, rods or tubes form light pipes are coated with one or more thick or alternatively thin layers of luminescent material. Tb, Pr or other rare earth doped lanthanum oxysulfide which can be utilized as a film are examples.

In an embodiment of the present invention, a lamp can contain a tube, which contains within it a luminescent material in powder, liquid or other form.

In an embodiment of the present invention, a luminescent light pipe can be of any appropriate cross sectional shape and can be free standing or constructed on a substrate.

Luminescent material is defined as a material which can be activated to luminesce, including glass impregnated with rare earth dopants, glass impregnated with transmetal dopants, organic polymers impregnated with rare earth dopants, organic polymers impregnated with transmetal dopants, inorganic polymers impregnated with rare earth dopants, inorganic polymers impregnated with transmetal dopants, organic emitters, inorganic emitters, CRT phosphors, lamp phosphors and scintillating material. In various embodiments of the present invention, luminescent materials can include one or more combinations of the luminescent material. In various embodiments of the present invention, luminescence materials can include all of the lanthanides doped into lanthanum, yttrium, or gadolinium oxides or oxysulfides, or other phosphors and scintillators with suitable emissions. In various embodiments of the invention, these rare earth dopants are used to generate a wide range of colors based on available and known phosphor and scintillator chemistries. This wide range of colors matches the numerous widely accepted and commonly used fluorophors for bioanalytical applications. In various embodiments of the invention, the light pipe can emit intense UV through to IR emission. Table 3 identifies characteristics of a light source subsystem which enhance the performance for irradiating molecules present in a plurality of capillaries.

In various embodiments of the present invention, a lamp can be switched on and off rapidly so that a time varying excitation can be produced. In an embodiment of the present invention, the color of the excitation can also be rapidly varied. In an embodiment of the present invention, these rapid variations in excitation can be used in conjunction with time-based detection to increase system sensitivity. In an embodiment of the present invention, these rapid variations in excitation can be used to allow for the discrimination of differing numbers, types, or states of fluorescence targets.

In an embodiment of the present invention, the luminescent fibers of Pr doped YAG are excited (pumped) by an array of LEDs with strong emission at 450 nm. In an embodiment of the present invention, the pump source can be replaced with one or more similar devices such as other color LEDs, fluorescent lamps, semiconductor or solid-state lasers, arc lamps, or incandescent lamps.

In an embodiment of the present invention, a lamp operates through the process of spontaneous emission, which results in a much larger selection of available wavelengths than can be available for efficient stimulated emission (laser action).

TABLE 3

Performance Enhancing Characteristics of Light Source Subsystem

| Feature | Enabled Through | Advantage |
| --- | --- | --- |
| Bright/Powerful | Stable source material can be driven to produce high power in one or several wavelengths | Allows for excitation of numerous capillaries simultaneously, sufficient power to provide for excitation of few or many detection volumes |
| Separate | Individual light pipe to pump one or numerous Fl excitation wavelengths through each capillary | Increased specific fluorescence excitation to each capillary; Increased specific fluorescence emission from each capillary; Enhanced discrimination of signals from several capillaries |
| Simultaneous | Each light pipe pumping each capillary at the same time | Simultaneous analyses; Easy to implement multiplexed analyses; Increased speed of analyses; Increased throughput |
| Modulation | On/Off of one or more LED's modulates fluorescence emission strength | Rapid, reproducible and stable modulation of excitation; reproducible fluorescence signal from capillaries after On/Off; results in facile discrimination between fluorescence signal and background and/or noise; allows for facile multiplexed signal generation in time by modulation of source excitation |
| Sensitivity | Increased fluorescence emission strength to capillaries; combination with time based detection | Enhanced S/N; no need for electronic signal optimization |
| Source Stability | Attenuating or increasing the LED's output. | Feedback of lamp output used to drive voltage of LED to give constant power |
| Spectra Stability | Stability of spectral emission from the luminescent material for example rare earth doped glasses, transmetal doped glasses and organic emitters | Significantly more spectral stability than that of 1) a laser which typically has color balance shifts over time and 2) an arc lamp which is notoriously unstable |

TABLE 3-continued

Performance Enhancing Characteristics of Light Source Subsystem

| Feature | Enabled Through | Advantage |
|---|---|---|
| Defined | Choice of one or more rare earth dopants | Specific fluorescence emission is narrowly defined; Simultaneously or serially; Excite different emission output wavelengths that are not changing in time; Produces specific fluorescence excitation wavelengths wavelength |
| Variable | Choice of one or more rare earth dopants | Produces specific fluorescence excitation wavelengths; facilitates multipexed analyses |
| Durability | Inherent stability of luminescent source material | Long term drift and or decay in lamp output eliminated |
| Discrimination | Controlled modulation of excitation | Distinguish number, type, or state of fluorescence labeled molecules |
| Low Heat | Low heat generating LED's and low thermal output of luminescent source material | Reduced heat in apparatus. |

In addition to chromatography systems and reaction vessels, the light source envisaged in this invention can be adapted for use in a variety of life science research tools including microarray scanners, microtiter plate readers, DNA sequencers, PCR and Q-PCR instruments, fluorescent microscopes, flow cytometery instruments and total analysis systems in the form of lab on a chip devices, optical sensors, medical devices based on luminescence, and miniaturized readers for therapeutic and diagnostic applications.

The foregoing description of the various embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

Other features, aspects and objects of the invention can be obtained from a review of the figures and the claims.

Separate and Simultaneous Irradiation: the light source subsystem provides sufficient power to irradiate linear arrays and 2-D arrays of analysis wells or spots in parallel for high density applications.

Modulation: Simple electronics can be used to modulate the light source subsystem at MHz rates. This capability allows for their use in analyses conducted in ambient light conditions. Analyses can be performed that discriminate against background signals and produce enhanced signal to noise ratios.

Moisture and Temperature Insensitivity: This is particularly important for remote sensing applications. The light source subsystem is stable for a very broad range of environmental testing conditions.

Low Heat Production: Analytical complications associated with heat generated by non light source subsystem are eliminated. This is particularly important for biological analyses.

Stability and Robustness: The color purity and intensity of the light source subsystem light output doesn't change as a function of how intensely they are driven nor does it change over time.

Modulation rates up to and even exceeding MHz can be achieved by modulating the excitation source used to activate our glass. In an embodiment of the invention, LEDs are used to excite the luminescent material. Therefore, modulating the LED will result in modulation of the light source output. The circuitry for modulating an LED is well known and typically consists of a square wave, sinusoidal wave or a pulse generator. The output of the generator is then fed to a transistor amplifier circuit which drives the LED.

It is to be understood that other embodiments of the invention can be developed and fall within the spirit and scope of the invention and claims

What is claimed is:

1. A system for use in analyzing one or more analyte comprising:
    one or more light pipes for use in generating luminescence, wherein each light pipe includes
        an excitation source which provides excitation energy, and
        a luminescent material which acts as a secondary absorber of the excitation energy, and wherein the luminescent material, when excited by the excitation source, generates and emits luminescence through an exit region of the light pipe;
    relay optics which are used to
        direct the luminescence at one or more wavelengths, from the one or more light pipes, onto one or more analyte, and
        direct emitted light, from the one or more analyte as a reaction to the luminescence, onto one or more light detector; and
    wherein the emitted light is used to detect one or more of the presence or characteristics of the one or more analyte.

2. The system of claim 1, wherein the one or more analyte undergoes an electrochemical reaction prior to, during or after the luminescence.

3. The system of claim 1, further comprising the step of identifying a characteristic of the one or more analyte based on the detection of the light emitted from the one or more analyte.

4. The system of claim 1, further comprising a coupler for directing one or more flow of the one or more analyte into one or more detection volume, wherein the luminescence is directed onto the one or more detection volume and the light emitted by the one or more analyte is emitted from the one or more detection volume.

5. The system of claim 4, wherein the luminescence is simultaneously and separately directed to the one or more detection volume.

6. The system of claim 4, further comprising a coupling plate for separating the one or more analyte in the one or more flow while directing the one or more flow into the one or more detection volume.

7. The system of claim 6, wherein the separation of the one or more analyte is temporal with respect to the duration of time of the one or more flow and the one or more analyte is detected at one or more elapsed time.

8. The system of claim 7, further comprising identifying the one or more analyte based on detecting one or more of the characteristics selected from the group consisting of emitted light wavelength, difference in emitted light wavelength, emitted light intensity, difference in emitted light intensity, direction of emitted light, difference in direction of emitted light, temperature, temperature change, potential, potential change, number of molecules, change in number of molecules, time elapsed and change in elapsed time.

9. The system of claim 1, wherein each of the one or more light pipes comprises a plurality of excitation sources whose combined energy is absorbed by the luminescent material as a secondary absorber, which in turn generates the light pipe's radiated output or luminescence.

10. The system of claim 1, wherein the excitation source provides optical and/or electronic excitation energy, and wherein if electronic excitation is used the excitation can be either voltage or current based.

11. The system of claim 1, wherein the excitation source provides optical excitation energy in the form of radiation by photoluminescent, cathodoluminescent and/or electroluminescent sources, such as from an ultraviolet (UV) light source, light emitting diode (LED) source, or laser source.

12. The system of claim 1, wherein the luminescent material which acts as a secondary absorber comprises one or more of a crystalline material, or doped crystalline, glass, or plastic material which includes one or more inorganic or organic luminescent dopants or co-dopants.

13. The system of claim 1, wherein the luminescent material has a geometric cross section and length, such as a tube, rod, fiber, disk, slab, or other shape.

14. The system of claim 1, wherein the one or more light pipe simultaneously or sequentially generates luminescence at a plurality of wavelengths, for direction by the luminescence relay optics onto the one or more analyte.

15. The system of claim 1, wherein the one or more light pipe includes a luminescent material which is formed or constrained within the shape of a tube, rod, fiber, disk, slab, or other shape, and wherein the luminescent material is excited by an excitation source which is optically coupled to the light pipe and provides excitation energy in the form of radiation to the luminescent material, which then absorbs the radiation and emits luminescence through an end of the tube, rod, fiber, disk, slab, or other shape.

16. The system of claim 1, wherein the excitation source is a light source, and wherein the luminescent material is wrapped around or otherwise optically coupled to the light source, so that it receives excitation energy along its length, and emits the luminescence through its end.

17. The system of claim 1, wherein the excitation light source is an ultraviolet (UV) lamp, light-emitted diode (LED), laser, or other light-emitting source, and wherein the light output of which is used to excite the luminescent material in the light pipe.

18. The system of claim 1, wherein the luminescent material, when excited by the excitation source, generates and emits luminescence by absorption and secondary spontaneous emission.

19. The system of claim 1, wherein the one or more analyte present in a detection volume undergoes a reaction selected from the group consisting of a heterogeneous reaction and a homogeneous reaction.

20. The system of claim 1, wherein the luminescence relay optics and emission relay optics are combined to reflect luminescence that has passed over the one or more analyte back to the detector.

21. The system of claim 1, wherein a plurality of light pipes are connected in series.

22. The system of claim 1, wherein a plurality of light pipes are connected in parallel.

23. The system of claim 1, wherein the detection volume is selected from the group consisting of a well, micro-cuvette, a micro-titer plate, a micro-array chip, a capillary, a tube, a pore, a sensor, a fluidic chip and a detection volume of a free flowing stream.

24. The system of claim 1, wherein the emitted light is detected based on one or more properties of the light emitted selected from the group consisting of fluorescence, phosphorescence, absorbance, transmittance, scattering and luminescence.

* * * * *